US008961385B2

(12) United States Patent
Pilla et al.

(10) Patent No.: US 8,961,385 B2
(45) Date of Patent: Feb. 24, 2015

(54) DEVICES AND METHOD FOR TREATMENT OF DEGENERATIVE JOINT DISEASES WITH ELECTROMAGNETIC FIELDS

(75) Inventors: Arthur A. Pilla, Oakland, NJ (US); Andre' A. DiMino, Woodcliff Lake, NJ (US); Matthew E. Drummer, Fort Lee, NJ (US)

(73) Assignee: Ivivi Health Sciences, LLC, San Francisco, CA (US)

( * ) Notice: Subject to any disclaimer, the term of this patent is extended or adjusted under 35 U.S.C. 154(b) by 799 days.

(21) Appl. No.: 13/080,450

(22) Filed: Apr. 5, 2011

(65) Prior Publication Data

US 2011/0207989 A1 Aug. 25, 2011

Related U.S. Application Data

(63) Continuation-in-part of application No. 12/819,956, filed on Jun. 21, 2010, now abandoned, which is a continuation-in-part of application No. 12/772,002, filed on Apr. 30, 2010, which is a continuation of application No. 11/003,108, filed on Dec. 3, 2004, now Pat. No. 7,744,524.

(60) Provisional application No. 61/321,044, filed on Apr. 5, 2010, provisional application No. 61/326,582, filed on Apr. 21, 2010, provisional application No. 60/527,327, filed on Dec. 5, 2003.

(51) Int. Cl.
*A61N 2/04* (2006.01)
*A61N 1/40* (2006.01)
*A61N 2/02* (2006.01)
*A61N 2/00* (2006.01)

(52) U.S. Cl.
CPC .. *A61N 1/40* (2013.01); *A61N 2/02* (2013.01); *A61N 2/008* (2013.01)
USPC ............................................................ 600/14

(58) Field of Classification Search
USPC ........... 600/9–15; 607/2, 3, 44–46, 50, 51, 59
See application file for complete search history.

(56) References Cited

U.S. PATENT DOCUMENTS 1,233,841 A   7/1917   Butcher
2,130,758 A   9/1938   Rose
(Continued)

FOREIGN PATENT DOCUMENTS

CA   0608693        11/1960
CN   1052053 A      6/1991
(Continued)

OTHER PUBLICATIONS

Blackman et al.; Effects of ELF fields on calcium-ion efflux from brain tissue in vitro; Radiat Res; vol. 92(3); pp. 510-520; Dec. 1982.
(Continued)

*Primary Examiner* — Samuel Gilbert
(74) *Attorney, Agent, or Firm* — Shay Glenn LLP

(57) ABSTRACT

Described herein are devices and methods for treating degenerative joint diseases with electromagnetic fields using one or more waveforms that are configured to modulate $Ca^{2+}$ binding to calmodulin and thereby modulate calmodulin-dependent nitric oxide signaling within joint and other affected tissue for the purpose of reducing pain and inflammation, as well as enhancing the healing and regeneration of such tissue.

29 Claims, 11 Drawing Sheets

(56) References Cited

U.S. PATENT DOCUMENTS

| | | | |
|---|---|---|---|
| 2,276,996 | A | 3/1942 | Milinowski |
| 2,648,727 | A | 8/1953 | Rockwell |
| 3,043,310 | A | 7/1962 | Milinowski |
| 3,181,535 | A | 5/1965 | Milinowski |
| 3,270,746 | A | 9/1966 | Kendall et al. |
| 3,329,148 | A | 7/1967 | Kendall |
| 3,329,149 | A | 7/1967 | Kendall et al. |
| 3,800,802 | A | 4/1974 | Berry et al. |
| 3,890,953 | A | 6/1975 | Kraus et al. |
| 3,952,751 | A | 4/1976 | Yarger |
| 3,978,864 | A | 9/1976 | Smith |
| 4,028,518 | A | 6/1977 | Boudouris et al. |
| 4,105,017 | A | 8/1978 | Ryaby et al. |
| 4,197,851 | A | 4/1980 | Fellus |
| 4,266,532 | A | 5/1981 | Ryaby et al. |
| 4,305,115 | A | 12/1981 | Armitage |
| 4,315,503 | A * | 2/1982 | Ryaby et al. ............ 600/14 |
| 4,338,945 | A | 7/1982 | Kosugi et al. |
| 4,340,063 | A * | 7/1982 | Maurer ............ 607/46 |
| 4,374,482 | A | 2/1983 | Moore et al. |
| 4,428,366 | A | 1/1984 | Findl et al. |
| 4,454,882 | A | 6/1984 | Takano |
| 4,556,051 | A * | 12/1985 | Maurer ............ 600/14 |
| 4,616,629 | A | 10/1986 | Moore |
| 4,627,438 | A | 12/1986 | Liss et al. |
| 4,654,574 | A | 3/1987 | Thaler |
| 4,672,951 | A | 6/1987 | Welch |
| 4,674,482 | A | 6/1987 | Waltonen et al. |
| 4,793,325 | A | 12/1988 | Cadossi et al. |
| 4,829,984 | A | 5/1989 | Gordon |
| 4,889,526 | A | 12/1989 | Rauscher et al. |
| 4,926,881 | A | 5/1990 | Ichinomiya et al. |
| 4,993,413 | A | 2/1991 | McLeod et al. |
| 4,998,532 | A | 3/1991 | Griffith |
| 5,000,178 | A | 3/1991 | Griffith |
| 5,014,699 | A | 5/1991 | Pollack et al. |
| 5,123,898 | A | 6/1992 | Liboff et al. |
| 5,147,284 | A * | 9/1992 | Fedorov et al. ............ 600/9 |
| 5,181,902 | A | 1/1993 | Erickson et al. |
| 5,224,922 | A | 7/1993 | Kurtz |
| 5,338,286 | A * | 8/1994 | Abbott et al. ............ 600/14 |
| 5,370,680 | A | 12/1994 | Proctor |
| 5,386,837 | A | 2/1995 | Sterzer |
| 5,407,421 | A | 4/1995 | Goldsmith |
| 5,478,303 | A | 12/1995 | Foley-Nolan et al. |
| 5,480,373 | A | 1/1996 | Fischer et al. |
| 5,518,496 | A | 5/1996 | McLeod et al. |
| 5,584,863 | A | 12/1996 | Rauch et al. |
| 5,595,564 | A * | 1/1997 | Pinna ............ 600/14 |
| 5,718,246 | A | 2/1998 | Vona |
| 5,718,721 | A | 2/1998 | Ross |
| 5,723,001 | A | 3/1998 | Pilla et al. |
| 5,743,844 | A | 4/1998 | Tepper et al. |
| 5,778,894 | A | 7/1998 | Dorogi et al. |
| 5,792,209 | A | 8/1998 | Varner |
| 5,814,078 | A | 9/1998 | Zhou et al. |
| 5,877,627 | A | 3/1999 | Fischer et al. |
| 5,908,444 | A | 6/1999 | Azure |
| 5,951,459 | A | 9/1999 | Blackwell |
| 5,968,527 | A | 10/1999 | Litovitz |
| 5,990,177 | A | 11/1999 | Brown |
| 5,997,464 | A | 12/1999 | Blackwell |
| 6,004,257 | A | 12/1999 | Jacobson |
| 6,083,149 | A | 7/2000 | Wascher et al. |
| 6,086,525 | A | 7/2000 | Davey et al. |
| 6,099,459 | A | 8/2000 | Jacobson |
| 6,132,362 | A | 10/2000 | Tepper et al. |
| 6,149,577 | A | 11/2000 | Bouldin et al. |
| 6,155,966 | A | 12/2000 | Parker |
| 6,190,893 | B1 | 2/2001 | Shastri et al. |
| 6,200,259 | B1 | 3/2001 | March |
| 6,213,934 | B1 | 4/2001 | Bianco et al. |
| 6,231,528 | B1 | 5/2001 | Kaufman et al. |
| 6,234,953 | B1 | 5/2001 | Thomas et al. |
| 6,246,912 | B1 | 6/2001 | Sluijter et al. |
| 6,261,221 | B1 | 7/2001 | Tepper et al. |
| 6,261,831 | B1 | 7/2001 | Agee |
| 6,301,506 | B1 | 10/2001 | den Boer et al. |
| 6,321,120 | B1 | 11/2001 | Surbeck et al. |
| 6,334,069 | B1 | 12/2001 | George et al. |
| 6,418,345 | B1 | 7/2002 | Tepper et al. |
| 6,421,562 | B1 | 7/2002 | Ross |
| 6,424,863 | B1 | 7/2002 | Flock et al. |
| 6,434,426 | B1 | 8/2002 | Munneke et al. |
| 6,443,883 | B1 | 9/2002 | Ostrow et al. |
| 6,458,151 | B1 | 10/2002 | Saltiel |
| 6,458,157 | B1 | 10/2002 | Suaning et al. |
| 6,463,336 | B1 | 10/2002 | Mawhinney |
| 6,556,872 | B2 | 4/2003 | Hauck |
| 6,560,489 | B2 | 5/2003 | Hauck |
| 6,561,968 | B1 | 5/2003 | Dissing et al. |
| 6,569,654 | B2 | 5/2003 | Shastri et al. |
| 6,589,159 | B2 | 7/2003 | Paturu |
| 6,629,971 | B2 | 10/2003 | McDaniel |
| 6,648,812 | B2 | 11/2003 | Ardizzone |
| 6,675,047 | B1 | 1/2004 | Konoplev et al. |
| 6,678,562 | B1 | 1/2004 | Tepper et al. |
| 6,684,108 | B2 | 1/2004 | Surbeck et al. |
| 6,701,185 | B2 | 3/2004 | Burnett et al. |
| 6,839,589 | B2 | 1/2005 | Petlan |
| 6,844,378 | B1 | 1/2005 | Martin et al. |
| 6,919,205 | B2 | 7/2005 | Brighton |
| 6,934,580 | B1 | 8/2005 | Osorio et al. |
| 6,955,642 | B1 | 10/2005 | Simon |
| 7,010,353 | B2 | 3/2006 | Gan et al. |
| 7,022,506 | B2 | 4/2006 | Brighton et al. |
| 7,089,060 | B1 | 8/2006 | Fitzsimmons |
| 7,130,692 | B2 | 10/2006 | Brighton et al. |
| 7,160,241 | B1 | 1/2007 | Herbst |
| 7,175,587 | B2 | 2/2007 | Gordon et al. |
| 7,177,695 | B2 | 2/2007 | Moran |
| 7,177,696 | B1 | 2/2007 | Pandelisev |
| 7,215,995 | B2 | 5/2007 | Brighton et al. |
| 7,288,062 | B2 | 10/2007 | Spiegel |
| 7,333,858 | B2 | 2/2008 | Killian et al. |
| 7,419,474 | B2 | 9/2008 | Lee |
| 7,429,471 | B2 | 9/2008 | Brighton |
| 7,456,189 | B2 | 11/2008 | Himmelsbach et al. |
| 7,465,546 | B2 | 12/2008 | Brighton |
| 7,465,566 | B2 | 12/2008 | Brighton et al. |
| 7,520,849 | B1 | 4/2009 | Simon |
| 7,566,295 | B2 | 7/2009 | Giardino et al. |
| 7,740,574 | B2 | 6/2010 | Pilla et al. |
| 7,744,524 | B2 | 6/2010 | Pilla |
| 7,758,490 | B2 | 7/2010 | Pilla et al. |
| 7,896,797 | B2 | 3/2011 | Pilla et al. |
| 8,167,784 | B1 | 5/2012 | Honeycutt et al. |
| 2001/0007937 | A1 | 7/2001 | MacKin |
| 2001/0031906 | A1 | 10/2001 | Ishikawa et al. |
| 2001/0044643 | A1 | 11/2001 | Litovitz |
| 2002/0035358 | A1 | 3/2002 | Wang |
| 2003/0023283 | A1 | 1/2003 | McDaniel |
| 2003/0028072 | A1 | 2/2003 | Fischell et al. |
| 2003/0093028 | A1 | 5/2003 | Spiegel |
| 2003/0099979 | A1 | 5/2003 | Ohtani et al. |
| 2003/0125769 | A1 | 7/2003 | Brighton |
| 2003/0171640 | A1 | 9/2003 | Canedo |
| 2004/0176803 | A1 | 9/2004 | Whelan et al. |
| 2004/0176805 | A1 | 9/2004 | Whelan et al. |
| 2004/0176806 | A1 | 9/2004 | Markoll |
| 2004/0267333 | A1 | 12/2004 | Kronberg |
| 2005/0049640 | A1 | 3/2005 | Gurtner et al. |
| 2005/0059153 | A1 | 3/2005 | George et al. |
| 2005/0215842 | A1 | 9/2005 | Pilla et al. |
| 2005/0222625 | A1 | 10/2005 | Laniado et al. |
| 2005/0251229 | A1 | 11/2005 | Pilla et al. |
| 2006/0009825 | A1 | 1/2006 | Chiriaev et al. |
| 2006/0161226 | A1 | 7/2006 | McMickle |
| 2006/0206174 | A1 | 9/2006 | Honeycutt et al. |
| 2006/0212077 | A1 | 9/2006 | Pilla et al. |
| 2006/0293724 | A1 | 12/2006 | Kronberg et al. |
| 2007/0026514 | A1 | 2/2007 | Pilla et al. |
| 2007/0149901 | A1 | 6/2007 | Gordon et al. |
| 2007/0173904 | A1 | 7/2007 | Pilla |

(56) References Cited

U.S. PATENT DOCUMENTS

| | | |
|---|---|---|
| 2007/0282156 A1 | 12/2007 | Konings |
| 2007/0288072 A1 | 12/2007 | Pascual-Leone et al. |
| 2007/0299472 A1 | 12/2007 | Brighton |
| 2008/0039901 A1 | 2/2008 | Kronberg et al. |
| 2008/0058793 A1 | 3/2008 | Pilla et al. |
| 2008/0132971 A1 | 6/2008 | Pille et al. |
| 2008/0140155 A1 | 6/2008 | Pilla et al. |
| 2008/0200749 A1 | 8/2008 | Zheng et al. |
| 2008/0208287 A1 | 8/2008 | Palermo et al. |
| 2008/0217263 A1 | 9/2008 | Higgins et al. |
| 2008/0288035 A1 | 11/2008 | Gill et al. |
| 2009/0018613 A1 | 1/2009 | Brighton |
| 2009/0030476 A1 | 1/2009 | Hargrove |
| 2009/0043188 A1 | 2/2009 | Rauscher |
| 2009/0099623 A1 | 4/2009 | Bentwich |
| 2009/0105781 A1 | 4/2009 | Brighton |
| 2009/0216068 A1 | 8/2009 | Thomas et al. |
| 2010/0179373 A1 | 7/2010 | Pille et al. |
| 2010/0210893 A1 | 8/2010 | Pilla |
| 2010/0222631 A1 | 9/2010 | Pilla |
| 2011/0112352 A1 | 5/2011 | Pilla et al. |
| 2011/0152598 A1 | 6/2011 | Pilla et al. |
| 2011/0190849 A1 | 8/2011 | Faltys et al. |
| 2014/0046115 A1 | 2/2014 | Pilla |
| 2014/0046117 A1 | 2/2014 | Pilla |

FOREIGN PATENT DOCUMENTS

| | | |
|---|---|---|
| DE | 970276 | 9/1958 |
| EP | 543152 | 10/1992 |
| EP | 0500983 | 7/1995 |
| EP | 1167070 A1 | 1/2002 |
| FR | 748828 | 4/1933 |
| GB | 0604107 | 6/1948 |
| GB | 2162066 | 1/1986 |
| GB | 2400316 A | 10/2004 |
| JP | 03-523271 | 8/2003 |
| WO | WO 83/01742 A1 | 5/1983 |
| WO | WO 95/27533 | 10/1995 |
| WO | WO 96/11723 | 4/1996 |
| WO | WO 2004/108208 A2 | 12/2004 |
| WO | WO 2005/051306 A2 | 6/2005 |
| WO | WO 2009/155516 | 12/2009 |
| WO | WO 2010/067336 A2 | 6/2010 |
| WO | WO 2011/053607 A1 | 5/2011 |

OTHER PUBLICATIONS

Chiabrera et al.; Bioelectromagnetic Resonance Interactions: Endogenous Field and Noise. In "Interaction Mechanisms of Low-Level Electromagnetic Fields in Living Systems." Oxford University Press. 164.179; Dec. 1992.
Chiabrera et al.; Quantum dynamics of ions in molecular crevices under electromagnetic exposure; (Brighton C, Pollak S, editors); Electromagnetics in biology and medicine; San Francisco, USA; San Francisco Press; pp. 21-26; Jun. 1991.
Chiabrera et al.; The role of the magnetic field in the EM interaction with ligand binding; In: "Mechanistic Approaches to Interaction of Electric and Electromagnetic Fields With Living Systems;" Blank, Findl (eds); New York; Plenum Press; pp. 79-95; Oct. 31, 1987.
Ginsberg, A. J.; Ultrashort radio waves as a therapeutic agent. Med Record 140, 651-653 (Dec. 19, 1934).
Goligorsky et al.; Relationships between caveolae and eNOS: everything in proximity and the proximity of everything; Am J Physiol Renal Physiol; 283; pp. F1-F10; Jul. 2002.
Hart, F.; A quantum mechanical model for bioelectromagnetic resonance phenomena; J Bioelectr; vol. 9; pp. 1-7; Jan. 1990.
Itoh et al.; Accelerated wound healing of pressure ulcers by pulsed high peak power electromagnetic energy (Diapulse). Decubitus 4(1), pp. 24-5, 29-30, 32 & 34 (Feb. 1991).
Jones et al.; Low energy time varying electromagnetic field interactions with cellular control mechanisms; In: fMechanistic approaches to interactions of electric and electromagnetic fields with living systemsf; Blank, Findl (eds); Plenum Press; NY; pp. 389-97; Oct. 31, 1987.
Kimura et al.; Reciprical regulation between nitric oxide and vascular endothelial growth factor in angiogenesis; Acta Biochimica Polonica; vol. 50, No. 1; pp. 49-59; (year of publication is sufficiently earlier than the effective U.S. filing date and any foreign priority date) 2003.
Kjellbom et al.; Preparation and polypeptide composition of chlorophyll-free plasma membranes from leaves of light-grown spinach and barley; Physiol Plant; vol. 62; pp. 501-509; Dec. 1984.
Lednev, V.; Possible mechanism for the effect of weak magnetic fields on biological systems: Correction of the basic expression and its consequences; In: Electricity and magnetism in biology and medicine Blank (eds.); San Francisco, CA; San Francisco Press, Inc.; pp. 550-552; Oct. 1993.
Lednev, V.; Possible mechanism for the influence of weak magnetic fields on biological systems; Bioelectromagnetics; vol. 12; pp. 71-75; (year of publication is sufficiently earlier than the effective U.S. filing and any foreign priority date) 1991.
Liboff, et al.; Experimental evidence for ion cyclotron resonance mediation of membrane transport; In: Blank, Findl (eds.); Mechanical approaches to interactions of electric and electromagnetic fields with living systems; Blank, Findl (eds.); New York; Plenum Press; pp. 281-296; Oct. 31, 1987.
Nara, et al.; Fourier Transform Infrared Spectroscopic Study on the $Ca2+$-bound Coordination Structures of Synthetic Peptide Analogues of the Calcium-binding Site III of Troponin C; Biopolymers; vol. 82; issue 4; pp. 339-343; Jul. 2006.
Ohkubo et al.; Acute effects of static magnetic fields on cutaneous microcirculation in rabbits; In Vivo; vol. 11; pp. 221-226; May-Jun. 1997.
Okano et al.; Biphasic effects of static magnetic fields on cutaneous microcirculation in rabbits; Bioelectromagnetics; vol. 20(3); pp. 161-171; (year of publication is sufficiently earlier than the effective U.S. filing date and any foreign priority date) 1999.
Olbe at al.; The spinach plasma membrane $Ca2\flat$ pump is a 120-kDa polypeptide regulated by calmodulinbinding to a terminal region; Physiol Plantarum; vol. 103; pp. 35-44; May 1998.
Pilla; Electrochemical information and energy transfer in vivo; Proc. 7th IECEC;Washington, D.C.; American Chemical Society; pp. 761-64; (year of publication is sufficiently earlier than the effective U.S. filing date and any foreign priority date) 1972.
Pineros et al.; Calcium channels in higher plant cells: Selectivity, regulation, and pharmacology; J Exp Bot; vol. 48; special issue; pp. 551-577; Mar. 1997.
Ramundo-Orlando, et al.; Effect of Low Frequency, Low Amplitude Magnetic Fields on the Permeability of Cationic Liposomes Entrapping Carbonic Anhydrase I. Evidence for Charged Lipid Involvement; Bioelectromagnetics; vol. 21; pp. 491-498; Oct. 2000.
Sagan, L.; Epidemiological and laboratory studies of power frequency electric and magnetic fields; JAMA; vol. 268(5); pp. 625-629; Aug. 5, 1992.
Sarimov, et al.; Exposure to ELF Magnetic Field Tuned to Zn Inhibits Growth of Cancer Cells. Bioelectromagnetics; vol. 26; No. 8; pp. 631-638; Dec. 2005.
Sisken et al.; Prospects on clinical applications of electrical stimulation for nerve regeneration. J Cell Biochem 52, 404-409 (Apr. 1993).
Smith, S.; Calcium cyclotron resonance and diatom mobility; Bioelectromagnetics; vol. 8; pp. 215-227; (year of publication is sufficiently earlier than the effective U.S. filing date and any foreign priority date) 1987.
Teleman et al.; Kinetics of $Ca2+$ binding to calmodulin and its tryptic fragments studied by 43Ca-NMR. Biochim Biophys Acta 873, 204-13 (Sep. 1986).
Trillo et al.; Magnetic fields at resonant conditions for the hydrogen ion affect neurite outgrowth in PC-12 cells: a test of the ion parametric resonance model. Bioelectromagnetics 17, 10-20 (year of publication is sufficiently earlier than the effective U.S. filing date and any foreign priority date) (1996).
Weinstein, et al.; $Ca2+$-Binding and Structural Dynamics in the functions of Calmodulin; Ann. Rev. Physiol; vol. 56; pp. 213-236; Mar. 1994.

(56) References Cited

OTHER PUBLICATIONS

Weintraub, M.; Magnetic bio-stimulation in painful diabetic peripheral neuropathy: a novel intervention R a randomized double-placebo crossover study; Am J Pain Manag; vol. 9; pp. 8-17; Jan. 1, 1999.

Yumoto, et al.; Coordination Structures of Ca2+ and Mg2+ in Akazara Scallop Troponin C in Solution; Eur. J. Biochem; vol. 268(23); pp. 6284-6290; Dec. 2001.

Zhadin, et al.; Frequency and Amplitude Windows in the Combined Action of DC and Low Frequency AC Magnetic Fields on Ion Thermal Motion in a Macromolecule: Theoretical Analysis; Bioelectromagnetics; vol. 26; issue 4; pp. 323-330; May 2005.

Zhadin, et al.; Ion Cyclotron Resonance in Biomolecules; Biomed Sci; vol. 1; pp. 245-250; (year of publication is sufficiently earlier than the effective U.S. filing date and any foreign priority date) 1990.

Arendash et al.; Electromagnetic Field Treatment Protects Against and Reverses Cognitive Impairment in Alzheimer's Disease Mice. Journal of Alzheimer's Disease vol. 19, 191-210 (Jan. 2010).

Barger et al.; Microglial Activation by Alzheimer Amyloid Precursor Protein and Modulation by Apolipoprotein E. Nature; vol. 388; 878-881 (Aug. 1997).

Czosnyka, et al.; Montoring and Interpretation of Intracranial Pressure. J. Neurol Neurosurg Psychiatry; vol. 75, 813-821; (Jun. 2004).

Pilla et al.; U.S. Appl. No. 13/801,789 entitled "Apparatus and method for electromagnetic treatment," filed Mar. 13, 2013.

Albensi et al.; Diffusion and high resolution MRI of traumatic brain injury in rats: time course and correlation with histology. Exp Neurol 162, 61-72 (Mar. 2000).

Anderson et al.; Fluoro-jade B stains quiescent and reactive astrocytes in the rodent spinal cord. J Neurotrauma 20, 1223-31 (Nov. 2003).

Armonda et al.; Wartime traumatic cerebral vasospasm: recent review of combat casualties. Neurosurgery 59, 1215-25; discussion 1225 (Dec. 2006).

Arnold et al.; Nitric oxide activates guanylate cyclase and increases guanosine 3':5'-cyclic monophosphate levels in various tissue preparations. Proc Natl Acad Sci U S A 74, 3203-7 (Aug. 1977).

Auffray et al.; Blood monocytes: development, heterogeneity, and relationship with dendritic cells. Annu Rev Immunol 27, 669-92 (Jan. 2009).

Bassett et al.; Generation of electric potentials by bone in response to mechanical stress. Science 137, 1063-4 (Sep. 28, 1962).

Bassett, C. A.; Biological significance of piezoelectricity. Calc. Tiss. Res. 1, 252 (Dec. 1968).

Beaumont et al.; The effects of human corticotrophin releasing factor on motor and cognitive deficits after impact acceleration injury. Neurol Res 22, 665-73 (Oct. 2000).

Beaumont et al.; The impact-acceleration model of head injury: injury severity predicts motor and cognitive performance after trauma. Neurol Res 21, 742-54 (Dec. 1999).

Beck et al.; The Bioelectromagnetics Society (History of the first 25 years); eds. Shappard, A. and Blackman, C.; 46 pgs.; (mo. unavailable) 2004.

Becker, T. O.; The bioelectric factors in amphibian limb regeneration. J. Bone Joint Surg. 43A, 643 (Jul. 1961).

Bederson et al.; Nuclear magnetic resonance imaging and spectroscopy in experimental brain edema in a rat model. J Neurosurg 64, 795-802 (May 1986).

Belanger et al.; Cognitive sequelae of blast-related versus other mechanisms of brain trauma. J Int Neuropsychol Soc 15(1), 1-8 (Jan. 2009).

Blackman et al.; Action of 50 Hz magnetic fields on neurite outgrowth in pheochromocytoma cells. Bioelectromagnetics 14, 273-86 (mo. unavailable) (1993).

Borbely et al.; Pulsed high-frequency electromagnetic field affects human sleep and sleep electroencephalogram. Neurosci Lett 275, 207-10 (Nov. 19, 1999).

Bracken et al.; Administration of methylprednisolone for 24 or 48 hours or tirilazad mesylate for 48 hours in the treatment of acute spinal cord injury. Results of the Third National Acute Spinal Cord Injury Randomized Controlled Trial. National Acute Spinal Cord Injury Study. Jama 277, 1597-604 (May 28, 1997).

Bredt, D. S.; Nitric oxide signaling specificity-the heart of the problem. J Cell Sci 116, 9-15 (Jan. 2003).

Brighton et al.; Signal transduction in electrically stimulated bone cells. J Bone Joint Surg Am 83-A, 1514-23 (Oct. 2001).

Brighton, C. T.; The treatment of non-unions with electricity. J Bone Joint Surg Am 63, 847-51 (Jun. 1981).

Brooks et al.; Magnetic resonance spectroscopy in traumatic brain injury. J Head Trauma Rehabil 16, 149-64 (Apr. 2001).

Burton, T.; New Test for Brain Injury on Horizon, The Wall Street Journal, New York, (Jul. 20, 2010).

Cammermeyer, J.; I. An evaluation of the significance of the "dark" neuron. Ergeb Anat Entwicklungsgesch 36, 1-61 (mo. unavailable) (1962).

Canals et al.; Neurotrophic and neurotoxic effects of nitric oxide on fetal midbrain cultures. J Neurochem 76, 56-68 (Jan. 2001).

Canseven et al.; Effects of ambient ELF magnetic fields: variations in electrolyte levels in the brain and blood plasma; Gazi Tip Dergisi / Gazi Medical Journal; 16(3); pp. 121-127; Sep. 2005.

Casper et al.; Dopaminergic neurons associate with blood vessels in neural transplants. Exp Neurol 184, 785-93 (Dec. 2003).

Casper et al.; Enhanced vascularization and survival of neural transplants with ex vivo angiogenic gene transfer. Cell Transpl. 11, 331-349 (mo. unavailable) (2002).

Cederberg et al.; What has inflammation to do with traumatic brain injury? Childs Nerv Syst 26, 221-6 (Feb. 2010).

Cernak et al.; Cognitive deficits following blast injury-induced neurotrauma: possible involvement of nitric oxide. Brain Inj 15, 593-612 (Jul. 2001).

Cernak et al.; Traumatic brain injury: an overview of pathobiology with emphasis on military populations. J Cereb Blood Flow Metab 30, 255-66 (Feb. 2010).

Cernak et al.; Ultrastructural and functional characteristics of blast injury-induced neurotrauma. J Trauma 50, 695-706 (Apr. 2001).

Ciani et al.; Akt pathway mediates a cGMP-dependent survival role of nitric oxide in cerebellar granule neurones. J Neurochem 81, 218-28 (Apr. 2002).

Colomer et al.; Physiological roles of the Ca2+/CaM-dependent protein kinase cascade in health and disease. Subcell Biochem 45, 169-214 (mo. unavailable) (2007).

Cook et al.; Resting EEG is affected by exposure to a pulsed ELF magnetic field. Bioelectromagnetics 25, 196-203 (Apr. 2004).

Cook et al.; The effects of pulsed, high-frequency radio waves on the rate of osteogenesis in the healing of extraction wounds in dogs; Oral Sug.; 32(6); (Dec. 1971).

Cork et al.; Computer-aided analysis of polarized neurite growth. Effects of applied electrical fields on neuronal development. J Neurosci Methods 32, 45-54 (Apr. 1990).

Courtney et al.; A thoracic mechanism of mild traumatic brain injury due to blast pressure waves. Med Hypotheses 72, 76-83 (Jan. 2009).

Csuka et al.; IL-10 levels in cerebrospinal fluid and serum of patients with severe traumatic brain injury: relationship to IL-6, TNF-alpha, TGF-beta1 and blood-brain barrier function. J Neuroimmunol 101, 211-21 (Nov. 1999).

De Olmos et al.; Use of an amino-cupric-silver technique for the detection of early and semiacute neuronal degeneration caused by neurotoxicants, hypoxia, and physical trauma. Neurotoxicol Teratol 16, 545-61 (Nov. 1994).

Dixon et al.; A controlled cortical impact model of traumatic brain injury in the rat. J Neurosci Methods 39, 253-62 (Oct. 1991).

Dixon et al.; A fluid percussion model of experimental brain injury in the rat. J Neurosurg 67, 110-9 (Jul. 1987).

Edwards et al.; Final results of MRC CRASH, a randomised placebo controlled trial of intravenous corticosteroid in adults with head injury-outcomes at 6 months. Lancet 365, 1957-9 (Jun. 2005).

Elder et al.; Blast-related mild traumatic brain injury: mechanisms of injury and impact on clinical care. Mt Sinai J Med 76, 111-8 (Apr. 2009).

Elder et al.; Increased locomotor activity in mice lacking the low-density lipoprotein receptor. Behav Brain Res 191, 256-65 (Aug. 2008).

(56) References Cited

OTHER PUBLICATIONS

Fabre et al.; Antidepressant efficacy and cognitive effects of repetitive transcranial magnetic stimulation in vascular depression: an open trial. Int J Geriatr Psychiatry 19, 833-42 (Sep. 2004).

Farndale et al.; The action of pulsed magnetic fields on cyclic AMP levels in cultured fibroblasts. Biochim Biophys Acta 881, 46-53 (Mar. 19, 1986).

Farrarelli et al.; Breakdown in cortical effective connectivity during midazolam-induced loss of consciousness. Proc Natl Acad Sci U S A 107, 2681-6 (Feb. 9, 2010).

Fassbender et al.; Temporal profile of release of interleukin-1beta in neurotrauma. Neurosci Lett 284, 135-8 (Apr. 2000).

Faul et al.; Traumatic brain injury in the United States (Emergency department visits, hospitalization and deaths 2002-2006); U.S. Dept. of Health and Human Services, 74 pgs.; Mar. 2010.

Fetler et al.; Brain under surveillance: the microglia patrol. Science 309, 392-3 (Jul. 15, 2005).

Fitzsimmons et al.; A pulsing electric field (PEF) increases human chondrocyte proliferation through a transduction pathway involving nitric oxide signaling. J Orthop Res 26, 854-9 (Jun. 2008).

Foda et al.; A new model of diffuse brain injury in rats. Part II: Morphological characterization. J Neurosurg 80, 301-13 (Feb. 1994).

Foley-Nolan et al.; Pulsed high frequency (27MHz) electromagnetic therapy for persistent neck pain. A double blind, placebo-controlled study of 20 patients. Orthopedics 13, 445-51 (Apr. 1990).

Friedman et al.; Quantitative proton MRS predicts outcome after traumatic brain injury. Neurology 52, 1384-91 (Apr. 1999).

Fukada et al.; On the piezoelectric effect of bone. J Phys Soc Japan 12 (10), 1158-1162 (Oct. 1957).

Gaetz, M.; The neurophysiology of brain injury. Clin Neurophysiol 115, 4-18 (Jan. 2004).

Garthwaite et al.; Cyclic GMP and cell death in rat cerebellar slices. Neuroscience 26, 321-6 (Jul. 1988).

Gasparovic et al.; Decrease and recovery of N-acetylaspartate/creatine in rat brain remote from focal injury. J Neurotrauma 18, 241-6 (Mar. 2001).

Ghirnikar et al.; Inflammation in traumatic brain injury: role of cytokines and chemokines. Neurochem Res 23, 329-40 (Mar. 1998).

Glass et al.; Mechanisms underlying inflammation in neurodegeneration. Cell 140, 918-34 (Mar. 19, 2010).

Gona et al.; Effects of 60 Hz electric and magnetic fields on the development of the rat cerebellum. Bioelectromagnetics 14, 433-47 (mo. unavailable) (1993).

Goodwin et al.; A double-blind study of capacitively coupled electrical stimulation as an adjunct to lumbar spinal fusions(printed from online source). Spine 24(13), 1349-1357 (Jul. 1999).

Graeber et al.; New expression of myelomonocytic antigens by microglia and perivascular cells following lethal motor neuron injury. J Neuroimmunol 27, 121-32 (May 1990).

Greenebaum et al.; Effects of pulsed magnetic fields on neurite outgrowth from chick embryo dorsal root ganglia. Bioelectromagnetics 17, 293-302 (mo. unavailable) (1996).

Hellmich et al.; Dose-dependent neuronal injury after traumatic brain injury; Brain Research; 1044; pp. 144-154 (May 2005).

Hutchinson et al.; Inflammation in human brain injury: intracerebral concentrations of IL-1alpha, IL-1beta, and their endogenous inhibitor IL-1ra. J Neurotrauma 24, 1545-57 (Oct. 2007).

Ignarro et al.; Heme-dependent activation of guanylate cyclase by nitric oxide: a novel signal transduction mechanism. Blood Vessels 28, 67-73 (Nov.-Dec. 1991).

Ito et al.; Characterization of edema by diffusion-weighted imaging in experimental traumatic brain injury. J Neurosurg 84, 97-103 (Jan. 1996).

Jackson et al.; The demonstration of new human brain-specific proteins by high-resolution two-dimensional polyacrylamide gel electrophoresis. J Neurol Sci 49, 429-38; (Mar. 1981).

Jenrow et al.; Weak ELF magnetic field effects on hippocampal rhythmic slow activity. Exp Neurol 153, 328-34 (Oct. 1998).

Jokela et al.; Assessment of the magnetic field exposure due to the battery current of digital mobile phones. Health Phys 86, 56-66 (Jan. 2004).

Jortner, B. S.; The return of the dark neuron. A histological artifact complicating contemporary neurotoxicologic evaluation. Neurotoxicology 27, 628-34 (Jul. 2006).

Kamm et al.; The effect of traumatic brain injury upon the concentration and expression of interleukin-1beta and interleukin-10 in the rat. J Trauma 60, 152-7 (Jan. 2006).

Kanje et al.; Pretreatment of rats with pulsed electromagnetic fields enhances regeneration of the sciatic nerve. Bioelectromagnetics 14, 353-9 (mo. unavailable) (1993).

Kingham et al.; Microglial secreted cathepsin B induces neuronal apoptosis. J Neurochem 76, 1475-84 (Mar. 2001).

Knowles et al.; Nitric oxide synthases in mammals. Biochem J 298, 249-58 (Mar. 1994).

Kossmann et al.; Intrathecal and serum interleukin-6 and the acute-phase response in patients with severe traumatic brain injuries. Shock 4, 311-7 (Nov. 1995).

Kramarenko et al.; Effects of high-frequency electromagnetic fields on human EEG: a brain mapping study. Int J Neurosci 113, 1007-19 (Jul. 2003).

Lai et al.; Magnetic-field-induced DNA strand breaks in brain cells of the rat. Environ Health Perspect 112, 687-94 (May 2004).

Langlois et al.; The epidemiology and impact of traumatic brain injury: a brief overview. J Head Trauma Rehabil 21, 375-8 (Aug. 2006).

LeDoux, J.; Emotion: clues from the brain. Annu Rev Psychol 46, 209-35 (Jan. 1995).

Lee et al.; Nitric oxide in the healing wound: a time-course study. J Surg Res 101, 104-8 (Nov. 2001).

Lee et al.; Pulsed magnetic and electromagnetic fields in experimental achilles tendonitis in the rat: a prospective randomized study. Arch Phys Med Rehabil 78, 399-404 (Apr. 1997).

Lescot et al.; Temporal and regional changes after focal traumatic brain injury. J Neurotrauma 27, 85-94 (Jan. 2010).

Lighthall, J. W.; Controlled cortical impact: a new experimental brain injury model. J Neurotrauma 5, 1-15 (mo. unavailable) (1988).

Lincoln et al.; Low frequency of pathogenic mutations in the ubiquitin carboxy-terminal hydrolase gene in familial Parkinson's disease. Neuroreport 10, 427-9 (Feb. 1999).

Ling et al.; Explosive blast neurotrauma. J Neurotrauma 26, 815-25 (Jun. 2009).

Linovitz et al.; Combined magnetic fields accelerate and increase spine fusion: a double-blind, randomized, placebo controlled study(printed from online source). Spine 27, 1383-1389 (Jul. 2002).

Liu et al.; Ubiquitin C-terminal hydrolase-L1 as a biomarker for ischemic and traumatic brain injury in rats (Author Manuscript). Eur J Neurosci 31(4), 722-32 (Feb. 2010).

Louin et al.; Selective inhibition of inducible nitric oxide synthase reduces neurological deficit but not cerebral edema following traumatic brain injury. Neuropharmacology 50, 182-90 (Feb. 2006).

Maas et al.; Moderate and severe traumatic brain injury in adults. Lancet Neurol 7, 728-41 (Aug. 2008).

Maas et al.; Prognosis and clinical trial design in traumatic brain injury: The IMPACT study. J Neurotrauma 24, 232-8 (Feb. 2007).

Maas et al.; Why have recent trials of neuroprotective agents in head injury failed to show convincing efficacy? A pragmatic analysis and theoretical considerations. (printed from online source) Neurosurgery 44, 1286-98 (Jun. 1999).

Madhusoodanan et al.; NO-cGMP signaling and regenerative medicine involving stem cells. Neurochem Res 32, 681-94 (Apr.-May 2007).

Maeda et al.; Effect of water on piezoelectric, dielectric, and elastic properties of bone; Biopolymers 21(10); 2055-2068 (Oct. 1982).

Marmarou et al.; A new model of diffuse brain injury in rats. Part I: Pathophysiology and biomechanics. J Neurosurg 80, 291-300 (Feb. 1994).

Martin et al.; Parkinson's disease alpha-synuclein transgenic mice develop neuronal mitochondrial degeneration and cell death. J Neurosci 26, 41-50 (Jan. 2006).

McFarlane et al.; Changes in neurite outgrowth but not in cell division induced by low EMF exposure: influence of field strength and culture

(56) References Cited

OTHER PUBLICATIONS conditions on responses in rat PC12 pheochromocytoma cells. Bioelectrochemistry 52, 23-8 (Sep. 2000).

McIntosh et al.; Traumatic brain injury in the rat: characterization of a lateral fluid-percussion model. Neuroscience 28(1), 233-44 (mo. unavailable) (1989).

McIntosh et al.; Traumatic brain injury in the rat: characterization of a midline fluid-percussion model. Cent Nery Syst Trauma 4, 119-34 (mo. unavailable) (1987).

Mellor, S.; The pathogenesis of blast injury and its management. Br J Hosp Med 39, 536-9 (Jun. 1988).

Mont et al.; Pulsed electrcial stimulation to defer TKA in patients with knee osteoarthritis; The Cutting Edge; 29(10); pp. 887-892 (Oct. 2006).

Morganti-Kossmann et al.; Production of cytokines following brain injury: beneficial and deleterious for the damaged tissue. Mol Psychiatry 2, 133-6 (Mar. 1997).

Morris et al.; Place navigation impaired in rats with hippocampal lesions. Nature 297, 681-3 (Jun. 1982).

Naldini et al.; Role of inflammatory mediators in angiogenesis. Curr Drug Targets Inflamm Allergy 4, 3-8 (Feb. 2005).

Narayan et al.; Clinical trials in head injury (Author Manuscript). J Neurotrauma 19, 503-57 (May 2002).

Nauta et al.; Silver impregnation of degenerating axons in the central nervous system: a modified technic. Stain Technol 29, 91-3 (Mar. 1954).

Northington et al.; Early Neurodegeneration after Hypoxia-Ischemia in Neonatal Rat is Necrosis while Delayed Neuronal Death Is Apoptosis. Neurobiol Dis 8, 207-19 (Apr. 2001).

Oda et al.; Magnetic field exposure saves rat cerebellar granule neurons from apoptosis in vitro. Neurosci Lett 365, 83-6 (Jul. 22, 2004).

Okie, S.; Traumatic brain injury in the war zone. N Engl J Med 352, 2043-7 (May 19, 2005).

Pantazis et al.; The nitric oxide-cyclic GMP pathway plays an essential role in both promoting cell survival of cerebellar granule cells in culture and protecting the cells against ethanol neurotoxicity. J Neurochem 70, 1826-38 (May 1998).

Papa et al.; Ubiquitin C-terminal hydrolase is a novel biomarker in humans for severe traumatic brain injury. Crit Care Med 38, 138-44 (Jan. 2010).

Pascual et al.; Time course of early metabolic changes following diffuse traumatic brain injury in rats as detected by (1)H NMR spectroscopy. J Neurotrauma 24, 944-59 (Jun. 2007).

Patino et al.; Pulsed electromagnetic fields in experimental cutaneous wound healing in rats. J Burn Care Rehabil 17, 528-31 (Nov./Dec. 1996).

Paylor et al.; Inbred strain differences in prepulse inhibition of the mouse startle response. Psychopharmacology (Berl) 132, 169-80 (Jul. 1997).

Pennington et al.; Pulsed, non-thermal, high-frequency electromagnetic energy (DIAPULSE) in the treatment of grade I and grade II ankle sprains. Mil Med 158, 101-4 (Feb. 1993).

Pfeffer et al.; Disturbed sleep/wake rhythms and neuronal cell loss in lateral hypothalamus and retina of mice with a spontaneous deletion in the ubiquitin carboxyl-terminal hydrolase L1 gene. Neurobiol Aging 33, 393-403, in press, Epub ahead of print (Apr. 2010).

Pilla et al.; Gap junction impedance tissue dielectrics and thermal noise limits for electromagnetic field bioeffects; Bioelectrochemistry and Bioenergetics; vol. 35; pp. 63-69; Nov. 1994.

Pilla, A.; Mechanisms and therapeutic applications of time-varying and static magnetic fields; In: Biological and Medical Aspects of Electromagnetic Fields (eds. Barnes et al.) CRC Press, Boca Raton FL, 351-411 (Oct. 2006).

Pirozzoli et al.; Effects of 50 Hz electromagnetic field exposure on apoptosis and differentiation in a neuroblastoma cell line. Bioelectromagnetics 24, 510-6 (Oct. 2003).

Reale et al.; Modulation of MCP-1 and iNOS by 50-Hz sinusoidal electromagnetic field. Nitric Oxide 15, 50-7 (Aug. 2006).

Ren et al.; Role of interleukin-1? during pain and inflammation (Author Manuscript). Brain Res Rev 60, 57-64 (Apr. 2009).

Rich et al.; Chronic caloric restriction reduces tissue damage and improves spatial memory in a rat model of traumatic brain injury. J Neurosci Res 88, 2933-9 (Oct. 2010).

Rogers et al.; Behavioral and functional analysis of mouse phenotype: SHIRPA, a proposed protocol for comprehensive phenotype assessment. Mamm Genome 8, 711-3 (Oct. 1997).

Rohde et al.; Effects of pulsed electromagnetic fields on interleukin-1 beta and postoperative pain: a double-blind, placebo-controlled, pilot study in breast reduction patients. Plast Reconstr Surg 125, 1620-9 (Jun. 2010).

Saljo et al.; Exposure to short-lasting impulse noise causes microglial and astroglial cell activation in the adult rat brain. Pathophysiology 8, 105-111 (Dec. 2001).

Saljo et al.; Low-level blast raises intracranial pressure and impairs cognitive function in rats: prophylaxis with processed cereal feed. J Neurotrauma 27, 383-9 (Feb. 2010).

Salzberg et al.; The effects of non-thermal pulsed electromagnetic energy on wound healing of pressure ulcers in spinal cord-injured patients: a randomized, double-blind study. Ostomy Wound Manage 41, 42-4, 46, 48 passim (Apr. 1995).

Sandyk, R.; Treatment with AC pulsed electromagnetic fields improves olfactory function in Parkinson's disease. Int J Neurosci 97, 225-33 (Apr. 1999).

Sapolsky; Glucocorticoid toxicity in the hippocampus: temporal aspects of neuronal vulnerability. Brain Res 359, 300-5 (Dec. 16, 1985).

Sauerland et al.; Risks and benefits of preoperative high dose methylprednisolone in surgical patients: a systematic review. Drug Saf 23, 449-61 (Nov. 2000).

Schmued et al.; Fluoro-Jade: a novel fluorochrome for the sensitive and reliable histochemical localization of neuronal degeneration. Brain Res 751, 37-46 (Mar. 1997).

Seegers et al.; Activation of signal-transduction mechanisms may underlie the therapeutic effects of an applied electric field. Med Hypotheses 57, 224-30 (Aug. 2001).

Shupak et al.; Human exposure to a specific pulsed magnetic field: effects on thermal sensory and pain thresholds. Neurosci Lett 363, 157-62 (Jun. 10, 2004).

Slepko et al.; Progressive activation of adult microglial cells in vitro. Glia 16, 241-46 (Mar. 1996).

Stahel et al.; The role of the complement system in traumatic brain injury. Brain Res Brain Res Rev 27, 243-56 (Jul. 1998).

Steinberg et al.; Results of core decompression and grafting with and without electrical stimulation. Clin Orthop, 199-208 (Dec. 1989).

Tehranian et al.; Improved recovery and delayed cytokine induction after closed head injury in mice with central overexpression of the secreted isoform of the interleukin-1 receptor antagonist. J Neurotrauma 19, 939-51 (Aug. 2002).

Terpolilli et al.; The novel nitric oxide synthase inhibitor 4-amino-tetrahydro-L-biopterine prevents brain edema formation and intracranial hypertension following traumatic brain injury in mice. J Neurotrauma 26, 1963-75 (Nov. 2009).

Thurman et al.; The epidemiology of sports-related traumatic brain injuries in the United States: recent developments. J Head Trauma Rehabil 13, 1-8 (Apr. 1998).

Unterberg et al.; Edema and brain trauma. Neuroscience 129(4), 1021-9 (mo. unavailable) (2004).

Vianale et al.; Extremely low frequency electromagnetic field enhances human keratinocyte cell growth and decreases proinflammatory chemokine production. Br J Dermatol 158(6), 1189-96 (Jun. 2008).

Weissman et al.; Activation and inactivation of neuronal nitric oxide synthase: characterization of $Ca(2+)$-dependent [125I]Calmodulin binding. Eur J Pharmacol 435, 9-18 (Jan. 2002).

Wenk, G.; The nucleus basalis magnocellularis cholinergic system: one hundred years of progress; Neurobiology of Learning and Memory; 67(2); 85-95 (Mar. 1997).

Williams et al.; Characterization of a new rat model of penetrating ballistic brain injury. J Neurotrauma 22, 313-31 (Feb. 2005).

Yasuda, I.; Part III. Clinical Studies: Mechanical and electrical callus; Annals of the New York Academy of Sciences; vol. 238; pp. 457-465 (Oct. 1974).

(56) References Cited

OTHER PUBLICATIONS

Yu et al.; Effects of 60 Hz electric and magnetic fields on maturation of the rat neopallium. Bioelectromagnetics 14, 449-58 (mo. unavailable) (1993).
Zaloshnja et al.; Prevalence of long-term disability from traumatic brain injury in the civilian population of the United States, 2005. J Head Trauma Rehabil 23, 394-400 (Nov./Dec. 2008).
Ziebell et al.; Involvement of pro- and anti-inflammatory cytokines and chemokines in the pathophysiology of traumatic brain injury. Neurotherapeutics 7, 22-30 (Jan. 2010).
Zizic et al.; The treatment of osteoarthritis of the knee with pulsed electrical stimulation. J Rheumatol 22, 1757-61 (Sep. 1995).
DiMino et al.; U.S. Appl. No. 13/361,797 entitled "Method and devices for providing electromagnetic treatment in the presence of a metal-containing implant," filed Jan. 30, 2012.
Aaron et al.; Power frequency fields promote cell differentiation coincident with an increase in transforming growth factor-?1 expression; bioelectromagnetics; vol. 20; pp. 453-458; 1999.
Aaron et al.; The conservative treatment of osteonecrosis of the femoral head. A comparison of core decompression and pulsing electromagnetic fields; Clin. Orthopaed. Rel. Res.; vol. 249; pp. 209-218; 1989.
Adair; A physical analysis of the ion parametric resonance model; Bioelectromagnetics; vol. 19; pp. 181-191; 1998.
Adair; Comment: Analyses of Models of Ion Actions Under the Combined Action of AC and DC Magnetic Fields; Bioelectromagnetics; vol. 27; No. 4; pp. 332-334; 2006.
Adair; Criticism of Lednev's mechanism for the influence of weak magnetic fields on biological systems; Bioelectromagnetics; vol. 13; pp. 231-235; 1992.
Adair; Static and low-frequency magnetic field effects: Health risks and therapies; Rep Prog Phys; vol. 63; pp. 415-454; 2000.
Akai et al.; Effect of electrical stimulation on musculoskeletal systems: a meta-analysis of controlled clinical trials; Bioelectromagnetics; vol. 23; pp. 132-143; 2002.
Ayrapetyan et al.; Magnetic fields alter electrical properties of solutions and their physiological effects; Bioelectromagnetics; vol. 15; pp. 133-142; 1994.
Bassett et al.; A non-operative salvage of surgically-resistant pseudoarthroses and non-unions by pulsing electromagnetic fields; Clin Orthop; vol. 124; pp. 117-131; 1977.
Bawin et al.; Effects of modulated VHF fields on the central nervous system; Ann NY Acad Sci; vol. 247; pp. 74-81; 1975.
Bawin et al.; Sensitivity of calcium binding in cerebral tissue to weak environmental electric fields oscillating at low frequency; Proc Nat"l Acad Sci, USA; pp. 1999-2003; 1976.
Bearden Jr.; Quantitation of submicrogram quantities of protein by an improved protein-dye binding assay; Biochim Biophys Acta; vol. 533; pp. 525-529; 1978.
Belyaev et al.; Frequency-dependent Effects of ELF Magnetic Field on Cromatin Conformation in *Escherichia coli* Cells and Human Lymphocytes; Biochimica et Biophysica Acta; vol. 1526; pp. 269-276; 2001.
Binder et al.; Pulsed electromagnetic field therapy of persistent rotator cuff tendinitis: a double blind controlled assessment; Lancet; vol. 1 (8379); pp. 695-697; 1984.
Blackman et al.; A role for the magnetic field in the radiation induced efflux of calcium ions from brain tissue in vitro; Bioelectromagnetics; vol. 6; pp. 327-337; 1985.
Blackman et al.; Empirical test of an ion parametric resonance model for magnetic field interactions with PC-12 cells; Bioelectromagnetics; vol. 15: pp. 239-260; 1994.
Blackman et al.; Influence of electromagnetic fields on the efflux of calcium ions from brain tissue in vitro: A three-model analysis consistent with the frequency response up to 510 Hz; Bioelectromagnetics; vol. 9; pp. 215-227; 1988.
Blackman et al.; Multiple power-density windows and their possible origin; Bioelectromagnetics; vol. 10; pp. 115-128; 1989.
Blanchard et al.; Clarification and application of an ion parametric resonance model for magnetic field interactions with biological systems; Bioelectromagnetics; vol. 15; pp. 217-238; 1994.
Blank et al.; Do electromagnetic fields interact directly with DNA?; Bioelectromagnetics; vol. 18; pp. 111-115; 1997.
Blumenthal et al.; Effects of low-intensity AC and/or DC electromagnetic fields on cell attachment and induction of apoptosis; Bioelectromagnetics; vol. 18; pp. 264-272; 1997.
Cain; Stimulating Treatment; Orthopedic Technology Review; vol. 4; No. 4; pp. 31-34; 2002.
Chiabrera et al.; Effect of Lifetimes on Ligand Binding Modelled by the Density Operator; Bioelectrochemistry and Bioenergetics; vol. 30; pp. 35-42; 1993.
Clapham, D.; Calcium signaling; Cell; vol. 80; pp. 259-268; 1995.
Colbert et al.; Magnetic mattress pad use in patients with fibromyalgia: A randomized double-blind pilot study; J Back Musculoskeletal Rehab; vol. 13; 19-31; 1999.
Collacott et al.; Bipolar permanent magnets for the treatment of low back pain: A pilot study; JAMA; vol. 283; No. 10; pp. 1322-1325; Mar. 8, 2000.
Cox, J.; Interactive Properties of Calmodulin; Biochem J.; vol. 249; pp. 621-629; 1988.
Edmonds, D.; Larmor precession as a mechanism for the detection of static and alternating magnetic fields; Bioelectrochemistry and Bioenergetics; vol. 30; pp. 3-12; 1993.
Engström, S.; Dynamic properties of Lednev's parametric resonance mechanism; Bioelectromagnetics; vol. 17; pp. 58-70; 1996.
Fitzsimmons et al.; Combined magnetic fields increase net calcium flux in bone cells. Calcif. Tiss. Intl.; vol. 55; pp. 376-380; 1994.
Halle, B.; On the cyclotron resonance mechanism for magnetic field effects on transmembrane ion conductivity; Bioelectromagnetics; vol. 9; pp. 381-385; 1988.
Johansson, et al.; Brij 58, a polyoxethylene acyl ether, creates membrane vesicles of uniform sidedness: A new tool to obtain inside-out (cytoplasmic side-out) plasma membrane vesicle; Plant J.; vol. 7; pp. 165-173; 1995.
Kloth et al.; Effect of Pulsed Radio Frequency Stimulation on Wound Healing: A Double-Blind Pilot Clinical Study; in "Electricity and Magnetism in Biology and Medicine"; Bersani F, ed,, Plenum, New York; pp. 875-878; 1999.
Koch, et al.; Interaction between weak low-frequency magnetic fields and cell membranes; Bioelectromagnetics; vol. 24; pp. 39-402; 2003.
Körner et al.; Surface properties of right side-out plasma membrane vesicles isolated from barley roots and leaves; Plant Physiol.; vol. 79; pp. 72-79; 1985.
Lansdown et al.; Sequential changes in trace metal, metallothionein and calmodulin concentrations in healing skin wounds; J. Anat.; vol. 195; pp. 375-386; 1999.
Larsson et al.; Isolation of highly purified plant plasma membranes and separation of inside-out and rightside-out vesicles; Methods Enzymol; vol. 228; pp. 451-469; 1994.
Liboff, et al.; Geomagnetic cyclotron resonance in living cells; J Biol Phys; vol. 9; pp. 99-102; 1985.
Liboff, et al.; Kinetics of channelized membrane ions in magnetic fields; Bioelectromagnetics; vol. 9; pp. 39-51; 1988.
Likic et al.; Dynamics of Ca2+-saturated Calmodulin D129N Mutant Studied by Multiple Molecular Dynamics Simulations; Protein Sci; vol. 12; pp. 2215-2229; 2003.
Lukas, T.; A Signal Transduction Pathway Model Prototype II: Application to Ca21-Calmodulin Signaling and Myosin Light Chain Phosphorylatiori; Biophysical Journal; vol. 87; pp. 1417-1425; 2004.
Man, et al.; The influence of permanent magnetic field therapy on wound healing in suction lipectomy patients: A double-blind study; Plastic and Reconstructive Surgery; vol. 104; pp. 2261-2296; 1999 (printed Jul. 17, 2010).
Markov, et al.; Weak static magnetic field modulation of myosin phosphorylation in a cell-free preparation: Calcium dependence; Bioelectrochemistry and Bioenergetics; vol. 43; pp. 233,238; 1997.
McDonald, F.; Effect of static magnetic fields on osteoblasts and fibroblasts in-vitro; Bioelectomagnetics; vol. 14; pp. 187-96; 1993.
McLean, et al.; Blockade of sensory neuron action potentials by a static magnetic field in the 10 mT range; Bioelectromagnetics; vol. 16; pp. 20-32; 1995.

(56) References Cited

OTHER PUBLICATIONS

McLeod, et al.; Dynamic characteristics of membrane ions in multifield configurations of low-frequency electromagnetic radiation; Bioelectromagnetics; vol. 7; pp. 177-189; 1986.

Mehler, et al.; Structural Dynamics of Calmodulin and Troponin C; Protein Engineering; vol. 4; No. 6; pp. 625-627; 1991.

Mooney; A randomized double blind prospective study of the efficacy of pulsed electromagnetic fields for interbody lumbar fusions; Spine; vol. 15; pp. 708-715; 1990.

Muehsam et al.; Lorentz Approach to Static Magnetic Field Effects on Bound Ion Dynamics and Binding Kinetics: Thermal Noise Considerations; Bioelectromagnetics; vol. 17; pp. 89-99; 1996.

Muehsam et al.; Weak Magnetic Field Modulation of Ion Dynamics in a Potential Well: Mechanistic and Thermal Noise Considerations; Bioelectrochem Bioenergetics; vol. 28; pp. 355-365; 1994.

Muehsam, et al.; The sensitivity of cells and tissues to exogenous fields: effects of target system initial state; Bioelectrochemistry and Bioenergetics; vol. 48; pp. 35-42; 1999.

Pilla et al.; EMF signals and ion/ligand binding kinetics:prediction of bioeffective waveform parameters; Bioelectrochemistry and Bioenergetics; vol. 48; pp. 27-34; 1999.

Pilla; Electrochemical information transfer at living cell membrane; Ann. N.Y.Acad. Sci.; vol. 238; p. 149-170; 1974.

Pilla; Low-intensity electromagnetic and mechanical modulation of bone growth and repair: are they equivalent?; Journal of Orthopedic Sciences; vol. 7; pp. 420-428; 2002.

Pilla; State of the art in electromagnetic therapeutics: soft tissue applications; Electricity and Magnetism in Biology and Medicine; Bersani (ed.); Kluwer Academic/Plenum Publishers; pp. 871-874; 1999.

Pilla; Weak time-varying and static magnetic fields: from Mechanisms to therapeutic applications; Biological Effects of Electro Magnetic Fields; P. Stavroulakis, ed. Springer Veriag; pp. 34-75; 2003.

Ryaby et al.; The role of insulin-like growth factor in magnetic field regulation of bone formation. Bioelectrochem. Bioenergetics; vol. 35; pp. 87-91; 1994.

Sisken, et al.; Static magnetic fields and nerve regeneration (presentation abstract); Bioelectromagnetics Society; 21st Ann Meeting, Long Beach, Jun. 20-24, 1999.

Valbona, et al.; Response of pain to static magnetic fields in post-polio patients: A doubleblind pilot study; Arch. Phys. Med. Rehabil.; vol. 78; pp. 1200-1203; 1997.

Weaver, et al.; The response of living cells to very weak electric fields: The thermal noise limit; Science; vol. 247; pp. 459-462; 1990.

Zdeblick; A prospective, randomized study of lumbar fusion: preliminary results; Spine; vol. 18; pp. 983-991; 1993.

Zhadin, M.; Combined action of static and alternating magnetic fields on ion motion in a macromolecule; Theoretical aspects; Bioelectromagnetics; vol. 19; pp. 279-292; 1998.

Zhuang et al.; Electrical stimulation induces the level of TGF-B 1 mRNA in osteoblastic cells by amechanism involving calcium/calmodulin pathway; Biochem. Biophys. Res. Comm.; vol. 237;pp. 225-229; 1997.

Pilla et al.; U.S. Appl. No. 13/252,114 entitled "Method and apparatus for electromagnetic treatment of head, cerebral and neural injury in animals and humans," filed Oct. 2, 2011.

Pilla, Arthur A.; U.S. Appl. No. 13/285,761 entitled "Method and apparatus for electromagnetic enhancement of biochemical signaling pathways for therapeutics and prophylaxis in plants, animals and humans," filed Oct. 31, 2011.

Pilla et al.; U.S. Appl. No. 14/354,587 entitled "Method and apparatus for electromagnetic treatment of cognition and neurological injury," filed Apr. 27, 2014.

Clausen et al.; Neutralization of interleukin-1 beta modifies the inflammatory response and improves histological and cognitive outcome following traumatic brain injury in mice. European Journal of Neuroscience; vol. 30; pp. 385-396; Aug. 30, 2009.

Pilla et al.; U.S. Appl. No. 14/171,553 entitled "Apparatus and method for electromagnetic treatment of neurological injury or condition caused by a stroke," filed Feb. 3, 2014.

Pilla et al.; U.S. Appl. No. 14/171,613 entitled "Apparatus and method for electromagnetic treatment of neurodegenerative conditions," filed Feb. 3, 2014.

Pilla et al.; U.S. Appl. No. 14/171,644 entitled "Apparatus and method for electromagnetic treatment of neurological pain," filed Feb. 3, 2014.

\* cited by examiner

300

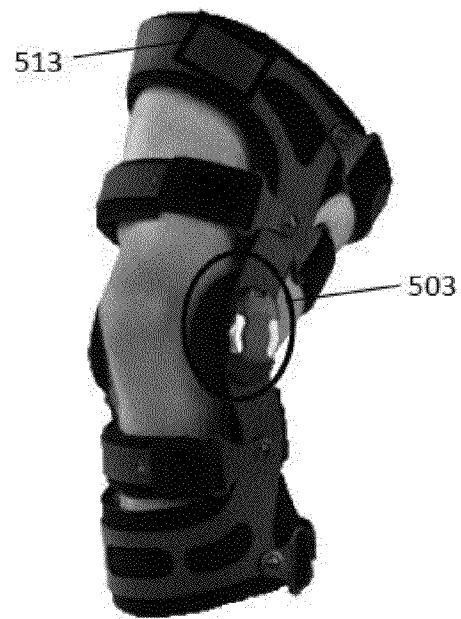
FIG. 5B
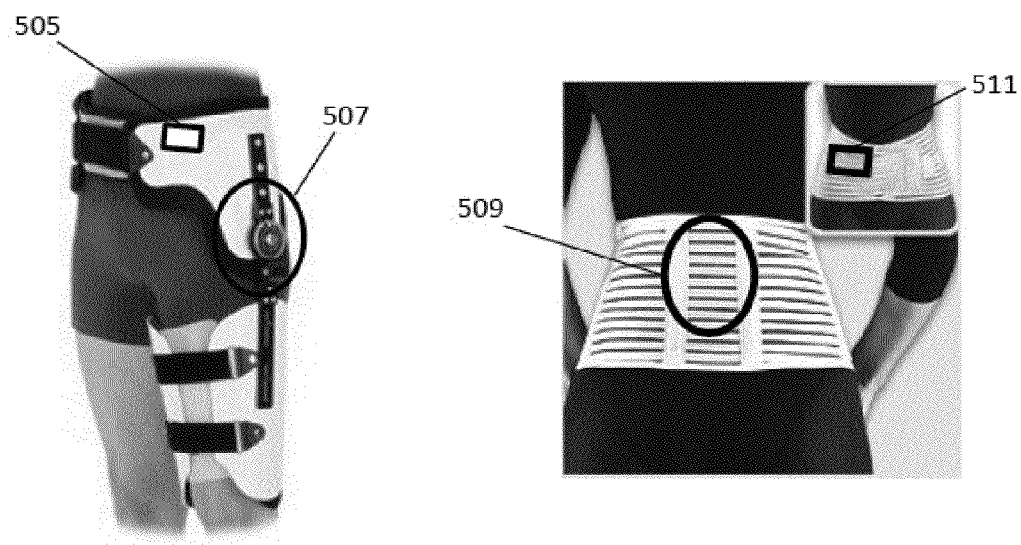
FIG. 5C
FIG. 5D

DEVICES AND METHOD FOR TREATMENT OF DEGENERATIVE JOINT DISEASES WITH ELECTROMAGNETIC FIELDS

CROSS REFERENCE TO RELATED APPLICATIONS

This patent application claims priority to U.S. Provisional Patent Application Nos. 61/321,044, filed Apr. 5, 2010, titled "DEVICES AND METHOD FOR TREATMENT OF OSTEOARTHRITIS BY ELECTRICAL STIMULATION" and 61/326,582, filed Apr. 21, 2010, titled "DEVICES AND METHOD FOR TREATMENT OF DEGENERATIVE JOINT DISEASES WITH ELECTROMAGNETIC FIELDS."

This patent application also claims priority as a continuation-in-part of pending U.S. patent application Ser. No. 12/819,956, filed Jun. 21, 2010, titled "APPARATUS AND METHOD FOR ELECTROMAGNETIC TREATMENT," which claims priority as a continuation-in-part of U.S. patent application Ser. No. 12/772,002, filed Apr. 30, 2010, titled "APPARATUS AND METHOD FOR ELECTROMAGNETIC TREATMENT OF PLANT, ANIMAL AND HUMAN TISSUE, ORGANS, CELLS AND MOLECULES," which is a continuation of U.S. patent application Ser. No. 11/003,108, filed Dec. 3, 2004, titled "APPARATUS AND METHOD FOR ELECTROMAGNETIC TREATMENT OF PLANT, ANIMAL, AND HUMAN TISSUE, ORGANS, CELLS, AND MOLECULES," which claims the benefit under 35 U.S.C. §119 of U.S. Provisional Patent Application No. 60/527,327, tiled Dec. 5, 2003, titled "APPARATUS AND METHOD FOR ELECTROMAGNETIC TREATMENT OF PLANT, ANIMAL, AND HUMAN TISSUE, ORGANS, CELLS AND MOLECULES." Each of these patents and pending patent applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

This invention pertains generally to electromagnetic devices and methods for delivering shaped and calibrated electromagnetic signals to promote cell and tissue growth, repair, and maintenance. In particular, the devices and methods described herein are intended and adapted to treat degenerative joint diseases ("DJD"), including osteoarthritis ("OA"), rheumatoid arthritis ("RA") and spondyloarthritis (SpA"), collectively known as arthritis.

BACKGROUND OF THE INVENTION

Chronic joint diseases are a major health problem. The economic burden caused by progressive morbidity, loss of function and disability of these diseases is a challenge to society. The outcome and severity of OA, RA and SpA diseases is determined by the balance in the joint between destructive and homeostatic or reparative pathways. The players in DJD include pro-inflammatory cytokines such as interleukin-1 (IL-1) and tumor necrosis factor-a (TNF-a), prostaglandins, tissue destructive enzymes such as matrix metalloproteinases (MMP) and cathepsins and cells such as osteoclasts. The ultimate goal of treatment in DJD and all chronic diseases is not only the inhibition of excessive tissue destruction, but also restoration of homeostasis and eventually tissue repair.

It is well-established that application of weak, non-thermal electromagnetic fields ("EMF") can result in physiologically meaningful in vivo and in vitro bioeffects. Time-varying electromagnetic fields, comprising rectangular waveforms, such as pulsing electromagnetic fields ("PEMF"), and sinusoidal waveforms, such as pulsed radio frequency fields ("PRF") ranging from several Hertz to an about 100 MHz range, are clinically beneficial when used as an adjunctive therapy for a variety of musculoskeletal injuries and conditions.

Beginning in the 1960's, development of modern therapeutic and prophylactic devices was stimulated by clinical problems associated with non-union and delayed union bone fractures. Early work showed that an electrochemical pathway can be a means through which bone adaptively responds to mechanical input. Early therapeutic devices used implanted and semi-invasive electrodes delivering direct current ("DC") to a fracture site. Non-invasive technologies were subsequently developed using capacitively and inductively coupled. electromagnetic fields. These modalities were originally created to provide anon-invasive "no-touch" means of inducing an electrical/mechanical waveform at a cell/tissue level. Clinical applications of these technologies in orthopaedics have led to approved applications by regulatory bodies worldwide for treatment of fractures such as non-unions and fresh fractures, as well as spine fusion. Presently several EMF devices constitute the standard armamentarium of orthopaedic clinical practice for treatment of difficult to heal fractures. The success rate for these devices has been very high. The database for this indication is large enough to enable its recommended use as a safe, non-surgical, non-invasive alternative to a first bone graft. Additional clinical indications for these technologies have been reported in double blind studies for treatment of avascular necrosis, tendinitis, osteoarthritis, wound repair, blood circulation and pain from arthritis as well as other musculoskeletal injuries.

Cellular studies have addressed effects of weak, low frequency electromagnetic fields on both signal transduction pathways and growth factor synthesis. It can be shown that EMF stimulates secretion of growth factors after a short, trigger-like duration. Ion/ligand binding processes at a cell membrane are generally considered an initial EMF target pathway structure. The clinical relevance to treatments of bone repair, for example, is upregulation such as modulation of growth factor production as part of normal molecular regulation of bone repair. Cellular level studies have shown effects on calcium ion transport, cell proliferation, Insulin Growth Factor ("IGF-II") release, and IGF-II receptor expression in osteoblasts. Effects on Insulin Growth Factor-I ("IGF-I") and IGF-II have also been demonstrated in rat fracture callus. Stimulation of transforming growth factor beta ("TGIF-β") messenger RNA ("mRNA") with PEMF in a bone induction model in a rat has been shown. Studies have also demonstrated upregulation of TGF-β mRNA by PEMF in human osteoblast-like cell line designated. MG-63, wherein there were increases in TGIF-β1, collagen, and osteocalcin synthesis. PEMF stimulated an increase in TGIF-β1 in both hypertrophic and atrophic cells from human non-union tissue. Further studies demonstrated an increase in both TGF-β1 mRNA and protein in osteoblast cultures resulting from a direct effect of EMF on a calcium (Ca)/calmodulin (CaM)-dependent pathway, Cartilage cell studies have shown similar increases in TGF-β1 mRNA and protein synthesis from PEMF, demonstrating a therapeutic application to joint repair. More recently it has been shown that. PEMF can modulate CaM-dependent nitric oxide (NO) signaling. U.S. Pat. No. 4,315,503 (1982) to Ryaby and U.S. Pat. No. 5,723,001 (1998) to Pilla typify the research conducted in this field.

However, prior art in this field has not produced electromagnetic signals configured specifically to accelerate the asymmetrical kinetics of the binding of intracellular ions to their associated buffers which regulate the biochemical signaling pathways living systems employ for growth, repair and maintenance, The result is that application of prior art devices, such as BGS devices and PRF devices, requires excessively long treatment times with associated prolonged patient morbidity, equivocal outcomes, and unnecessarily higher health care expenses. Prior art in this field also typically required devices which use unnecessarily high amplitude and power to induce a PEMF signal to a target pathway structure, required unnecessarily long treatment time, and were not portable.

Therefore, a need exists for an apparatus and a method that more effectively modulates biochemical processes that regulate tissue growth and repair, shortens treatment times, and incorporates miniaturized circuitry and light weight applicators thus allowing the apparatus to be portable and, if desired, disposable. A further need exists for an apparatus and method that more effectively modulates biochemical processes that regulate tissue growth and repair, shortens treatment times, and incorporates miniaturized circuitry and light weight applicators that can be constructed to be implantable. A further need exists for an apparatus and method that incorporates the asymmetrical kinetics of ion binding to intracellular buffers to configure electromagnetic waveforms to increase the rate of ion binding and enhance the biochemical signaling pathways living systems employ for growth, repair and maintenance. In particular, there is a need to treat DJD at the level of the joint and affected tissue, using a portable, wearable, lightweight device/apparatus capable of effecting tissue growth and repair. Described herein are devices that may meet the needs described above.

SUMMARY OF THE INVENTION

The present invention relates to the treatment of DJD by the application of electromagnetic signals to joints and other regions to prevent, cure, and/or alleviate DJD or symptoms of DJD (generally referred to as "treating arthritis"), Described herein are weak electromagnetic field devices and methods designed to reduce pain from arthritis and achieve joint and affected tissue regeneration.

In particular, an embodiment according to the present invention pertains to use of non-thermal static and time-varying electromagnetic fields configured to accelerate the asymmetrical kinetics of the binding of intracellular ions to their respective buffers which regulate the biochemical signaling pathways living systems employ for growth, repair and maintenance. Another embodiment according to the present invention pertains to the non-thermal application of repetitive pulse bursts of bipolar sinusoidal, rectangular, chaotic or arbitrary waveform electromagnetic fields to instantaneously accelerate ion-buffer binding in signaling pathways in structures such as molecules, cells, tissues, organs, and entire organisms of plants, animals or humans using ultra lightweight portable coupling devices such as inductors and electrodes, driven by miniature signal generator circuitry that can be incorporated into an anatomical positioning device such as a dressing, bandage, compression bandage, compression dressing, knee, elbow, lumbar or cervical back, shoulder, foot, head, neck and other body portion wraps.

Yet another embodiment according to the present invention pertains to application of bipolar sinusoidal, rectangular, chaotic or arbitrary waveform electromagnetic signals, having frequency components below about 100 GHz, configured to accelerate the binding of intracellular $Ca^{2+}$ to a buffer, such as calmodulin (hereinafter known as CaM), to enhance biochemical signaling pathways in target structures such as plant, animal and human molecules, cells, tissues, organs, portions of entire organisms and entire organisms. Signals configured according to embodiments of the present invention produce a net increase in a bound ion, such as $Ca^{2+}$ at CaM binding sites because the asymmetrical kinetics of Ca/CaM binding allows such signals to accumulate voltage induced at the ion binding site, thereby accelerating voltage-dependent ion binding. Examples of therapeutic and prophylactic applications of the present invention are modulation of biochemical signaling in anti-inflammatory pathways, modulation of biochemical signaling in cytokine release pathways, modulation of biochemical signaling in growth factor release pathways; chronic and acute musculoskeletal pain relief; edema and lymph reduction, anti-inflammatory, post surgical and post operative pain and edema relief, nerve, bone and organ pain relief, increased local blood flow, microvascular blood perfusion, treatment of tissue and organ ischemia, cardiac tissue ischemia, brain tissue ischemia from stroke or traumatic brain injury, treatment of neurological injury and neurodegenerative diseases such as Alzheimer's and Parkinson's; wound repair, bone repair, tissue repair; osteoporosis treatment and prevention; degenerative bone disease treatment and prevention; angiogenesis, neovascularization; enhanced immune response; treatment of diabetes Types I and II; enhanced effectiveness of pharmacological agents; nerve regeneration, skeletal muscle regeneration, cardiac muscle regeneration; cancer treatment; prevention of apoptosis; modulation of heat shock proteins for prophylaxis and response to injury or pathology. An embodiment according to the present invention can also be used in conjunction with other therapeutic and prophylactic procedures and modalities such as heat, cold, light, ultrasound, mechanical manipulation, massage, physical therapy, vacuum assisted wound closure, wound dressings, orthopedic and other surgical fixation devices, and surgical interventions. Yet another embodiment according to the present invention can also be used in conjunction with all pharmacological agents. Another embodiment of the present invention can be used with imaging or non-imaging diagnostic procedures.

The applied electromagnetic signal may be configured specifically to treat DJD by using signal to noise ratio ("SNR") and/or power signal to noise ratio ("PSNR") approaches to configure bio-effective waveforms. The applied electromagnetic signal may also deliver bipolar electromagnetic signals configured specifically to accelerate the asymmetrical kinetics of the binding of intracellular ions to their respective intracellular buffers, to enhance the biochemical signaling pathways plant animal and human molecules, cells, tissues, organs, portions of entire organisms and entire organisms employ for growth, repair and maintenance, A preferred embodiment according to the present invention utilizes a repetitive burst of bipolar arbitrary non-thermal waveforms configured to maximize the bound concentration of intracellular ions at their associated molecular buffers to enhance the biochemical signaling pathways living systems employ for growth, repair and maintenance. Non-thermal electromagnetic waveforms are selected first by choosing the ion and the intracellular buffer, for example $Ca^{2+}$ and CaM, among the many ion-buffer combinations within the living cell, which determines the frequency range within which the signal must have non-thermal frequency components of sufficient, but non-destructive, amplitude to accelerate the kinetics of ion binding. Signals comprise a pulse duration, random signal duration or carrier period which is less than half of the ion bound time to increase the voltage in the target pathway so as to maximally accelerate ion binding to maximally modulate biochemical signaling pathways to enhance specific cellular and tissue responses to physical and chemical perturbations.

In preferred embodiments of the present invention, signals comprise bursts of at least one of sinusoidal, rectangular, chaotic or random wave shapes; have burst duration less than about 100 msec, with frequency content less than about 100 MHz, repeating at less than about 1000 bursts per second. Peak signal amplitude in the ion-buffer binding pathway is less than about 1000 V/m. One preferred embodiment according to the present invention comprises about a 10 to about a 50 millisecond burst of radio frequency sinusoidal waves in the range of about 1 to about 100 MHz, incorporating radio frequencies in the industrial, scientific and medical (hereinafter known as ISM) band, for example 27.12 MHz, but it may be 6.78 MHz, 13.56 MHz or 40.68 MHz in the short wave frequency band, repeating between about 0.1 and about 10 bursts/sec. Such waveforms can be delivered via inductive coupling with a coil applicator or via capacitive coupling with electrodes in electrochemical contact with the conductive outer surface of the target.

Also described herein are devices for delivery of these bio-effective waveforms to the joints or other related tissues. Any of these devices may include and incorporate miniaturized circuitry and lightweight flexible coils for delivery of the bio-effective waveforms described herein. These devices may be constructed as disposable, stand alone or may be integrated into one or more other braces, casts or prosthetic devices.

A device (or apparatus) for treating DJD typically induces pulsating electric currents in joints and affected tissue that may reduce pro-inflammatory cytokines and other pro-inflammatory pathways, and therefore, associated pain and inflammation directly in the joint or from affected bone, e.g., local bone marrow edema, and may slow or reverse the destruction of joint tissue, including cartilage. The induced currents may improve growth factor production, leading to the re-growth of joint tissue, including cartilage. These devices may be adapted to apply the electromagnetic waveforms to any joint or synovial/bone interface, but particularly joints of the knee, hip, and hand.

In general, these devices may be lightweight, portable, rechargeable and/or disposable, and may be anatomically fitted as stand-alone units or may be embedded within other products, to provide for manual or automatic treatment regimens.

In operation, these devices may be used to apply bio-effective waveforms (electromagnetic fields having a predetermined waveform as described herein) to one or more joints to be treated for DJD. The bio-effective waveform may be calculated and configured specifically to modify a biological pathway related to DJD; For example, the device may produce a pulsed electromagnetic signal (bio-effective waveform) that comprises a series of pulse or sinusoidal bursts. The pulses or sinusoids may have a specific duration, frequency and amplitude; further the bursts may themselves have a specific duration, frequency and amplitude.

Thus, a device may apply a signal that accelerates a specific electrochemical binding process with some specificity. In particular, the signal may modulate the binding of Ca to CaM in target tissue within the joint. By accelerating the process of Ca/CaM binding, the cascade of biochemical activity that follows may be likewise accelerated, and particularly modulating the local production of NO through activation of the constitutive nitric oxide synthases (cNOS) by modulation of CaM activation and then the increased production of growth factors to enhance healing in the joint and affected tissue, including cartilage, through the modulated production of cGMP and cAMP.

For example, a device as described herein can be configured so that it applies a bio-effective waveform for a predetermined amount of time using a predetermined (or modifiable) treatment regime. In one variation, the signal frequency within a particular burst envelope is centered on a particular carrier frequency (e.g., 27.12 MHz, 6.78 MHz, etc.). For example, the waveform within a burst may use a carrier frequency of 6.78 MHz and the frequency between bursts can be modulated by producing bursts at 1 Hz. In one variation, bursts are 7 ms in duration with a peak amplitude of 0.05 Gauss. In another example, a device can be configured using a carrier frequency of 27.12 MHz that can be modulated by producing a burst at 2 Hz, such bursts being 2 ms in duration with a peak amplitude of 0.05 Gauss.

In some variations, the device is configured to explicitly limit the peak signal strength of the applied signal. For example, the peak signal strength may be limited to approximately 50 milliGauss (e.g., 0.05 Gauss). A proper signal configuration to produce the necessary induced electric fields in the range of 0.1-100 millivolts percentimeter ("mV/cm") for a given carrier frequency may be determined as described herein. In general, the desired and specific effect seen on the target pathway (e.g., the Ca/CaM pathway) may be very sensitive to the waveform parameters. The ranges of waveform parameters described herein are tuned to the desired effect.

In addition, the treatment regime applied may be calibrated to the end effect. For example, in some variations, the treatment regime used to treat DJD may include: 15 minute applications twice a day. A 15 minute application may include 7 ms bursts applied at a frequency of about once a second (1 Hz), so the total time that therapeutic currents are delivered is about 8.1 seconds. Thus, the effective duty cycle of the applied current is extremely low (e.g., the total energy applied over time), and may be less than 1% (e.g., 0.9%) "on" time during the treatment on-time; one treatment may be followed by a 4-12 hour (or more) recovery time, so the mean energy applied to the tissue over time is even less. For example, to treat DJD, a patient may receive therapy over a day for approximately 1-60 minutes. That therapy may be delivered in a single 1 hour treatment, or as a series of 60, 1 minute treatments over a longer period.

In some variations, an electromagnetic signal generator (for emitting signals comprising bursts of the bio-effective signal) may be used, and may be part of the device or a system including the device. For example, the device may include a signal generator configured to generate the afore-mentioned bio-effective signal comprising at least one of sinusoidal, rectangular, chaotic, and random waveforms. The signal generator may have a frequency content in a range of about 0.01 Hz to about 100 MHz at about 1 to about 100,000 waveforms per second, having a burst duration from about 1 usec to about 100 msec, and a burst repetition rate from about 0.01 to about 1000 bursts/second, wherein the waveforms are configured to have sufficient SNR or PSNR of at least about 0.2 in respect of the target pathway within the target tissues of the joint or affected tissue to modulate ion and/or ligand interactions in that target tissue. When determining the bio-effective signal, the waveform may be configured using the signal to noise ratio, SNR, or PSNR as evaluated by calculating a frequency response of the impedance of the target path structure divided by the root mean square (RMS) of baseline thermal fluctuations in voltage across the target path structure, assuming the electromagnetic signal coupling device (the device) wherein the coupling device comprises an inductive coupling member and/or a capacitive coupling member, connected to the electromagnetic signal generator for delivering the electromagnetic signal to the target joint and affected tissue The electromagnetic signal generator and electromagnetic signal coupling device may be incorporated into a dressing, garment, orthotic, brace, or the like.

A device comprising a waveform configuration element (e.g., shaping the desired waveform based on the bio-effective signal determined) may include dedicated circuitry (e.g., hardware, software, firmware) or the like to time and emit the desired bio-effective waveform.

As mentioned, the bio-effective waveform may be determined in advance by configuring at least one waveform to have sufficient SNR or PSNR of at least about 0.2, but preferably greater than about 1, to modulate ion and/or ligand interactions whereby the increases in ion and/or ligand interactions in the target joint tissue are detectable above baseline thermal fluctuations in voltage, wherein SNR or PSNR may be evaluated by calculating a frequency response of the impedance of the target path structure divided by the RMS of baseline thermal fluctuations in voltage across the target path structure. A coupling device may be connected to the waveform configuration element by at least one connector for generating an electromagnetic signal from the configured at least one waveform and for coupling the electromagnetic signal to the target tissue, whereby the ion and/or ligand interactions may be modulated. As mentioned, a dressing, garment, brace, or the like may incorporate the device, which may include a waveform configuration element, and at least one connecting element (e.g., applicator).

The bio-effective waveform may be determined by establishing a baseline thermal fluctuation in voltage at a target tissue (e.g., joint) depending on a state of the target tissue, and evaluating SNR or PSNR by calculating a frequency response of the impedance of the target pathway structure divided by the RMS of baseline thermal fluctuations in voltage across the target pathway structure, configuring at least one waveform to have sufficient SNR or PSNR of at least about 0.2 to modulate ion and/or ligand interactions whereby the increases in ion and/or ligand interactions (e.g., Ca/CaM) are detectable in the target tissue and target pathway structure above the evaluated baseline thermal fluctuations in voltage. The bio-effective waveform may be applied to the target tissue (target pathway) using a coupling device (e.g., applicator) which may be incorporated into the brace, dressing, garment, orthotic, or the like.

The bio-effective waveform is further determined by configuring a repetitive burst of arbitrary non-thermal waveforms to maximize the bound concentration of intracellular ions at their associated molecular buffers to enhance the biochemical signaling pathways living systems employ for growth, repair and maintenance. Non-thermal electromagnetic waveforms are selected first by choosing the ion and the intracellular buffer, for example $Ca^{2+}$ and CaM, among the many ion-buffer combinations within the living cell, which determines the frequency range within which the signal must have non-thermal frequency components of sufficient, but non-destructive, amplitude to accelerate the kinetics of ion binding. Signals comprise a pulse duration, random signal duration or carrier period which is less than half of the ion bound time to increase the voltage in the target pathway so as to maximally accelerate ion binding to maximally modulate biochemical signaling pathways to enhance specific cellular and tissue responses to physical and chemical perturbations.

For example, described herein are methods of treating degenerative joint disease comprising: positioning a flexible coil wire applicator of a lightweight wearable or stationary pulsed EMF therapy device adjacent to a joint o issue to be treated; applying a treatment regime from the therapy device, wherein the treatment regime comprises bursts of electromagnetic waves having a peak amplitude of less than about 100 milliGauss, wherein the bursts have a duration of between about 0.5 msec and about 50 msec, further wherein the bursts are repeated at an interburst interval of between about 2 sec and 0.1 sec for a treatment on-time, followed by a treatment off-time that is greater than the treatment on-time.

The treatment regime may be configured according to a mathematical model, as described herein. For example, the mathematical model may include a signal to noise ratio (SNR) or power signal to noise ratio (PSNR) in respect to calmodulin-dependent NO signaling, and/or in respect to calmodulin-dependent signaling.

In general, the methods of treating degenerative joint disease may be methods of treatment of osteoarthritis, rheumatoid arthritis, spondyloarthritis, and/or generally arthritis.

The duty cycle of the treatment regime may be extremely low, particularly in comparison to other therapeutic device for treating degenerative joint diseases. For example, the treatment on-time may be between about 1 minute and about 60 minutes (e.g., between about 5 minutes and 15 minutes), or less, and the treatment on time may be about 1 hour to as long as 48 hours (e.g., 12 hours). During the on-time, the treatment regime is a repeated burst of pulses (e.g., sinusoidal, square waves, etc.) at a carrier frequency of 6.8 MHz, 27.12 MHz (or a harmonic of these), with a burst duration that is relatively short compared to the interburst interval.

In some variations, the devices and apparatus described herein are lightweight, wearable, battery-operated EMF therapy apparatus for treating degenerative joint disease which include: a flexible coil wire applicator coupled to battery-operated EMF therapy microcontroller within a lightweight, wearable housing; wherein the microcontroller is configured to drive the applicator to deliver bursts of electromagnetic waves having a peak amplitude of less than about 200 milliGauss, wherein the bursts have a duration of between about 0.5 msec and about 50 msec, further wherein the bursts are repeated at an interburst interval of between about 10 sec and 0.1 sec for a treatment on-time of between about 5 minutes and 30 minutes, followed by a treatment off-time that is greater than about 30 minutes. The microcontroller may be configured to drive the applicator to deliver bursts of 6.8 MHz sinusoidal electromagnetic waves having a peak amplitude of about 50 milliGauss, wherein the duration of the burst is about 7 msec, and bursts repeat approximately every second. In some variations, the apparatus includes (or is part of) a brace or garment incorporating the applicator.

In general, the flexible coil applicator may be a wire coil applicator, and particularly wire coil applicators having a loop diameter of between about 12 and about 5 inches (e.g., 6 inches, 7 inches, 8 inches, etc.). The applicator may be part of a brace, orthotic, garment, or the like, as described herein.

BRIEF DESCRIPTION OF THE DRAWINGS

FIGS. 5A-5D illustrate variations of devices described herein that may be used directly or placed in a various dressings, garments and/or orthotics, so that the device may be aligned with the target joint(s) or other affected tissue.

DETAILED DESCRIPTION OF THE INVENTION

Figure 1:
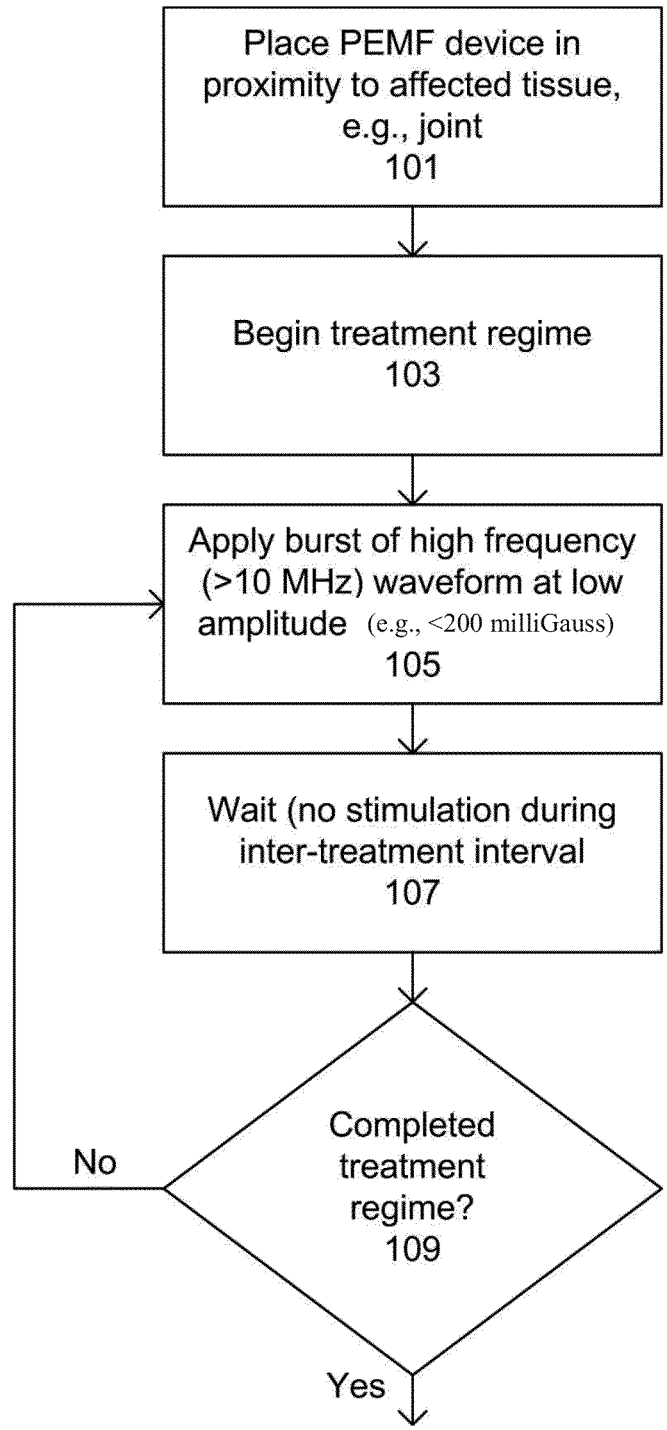
FIG. 1 is a flow diagram of a method for treating DJD (e.g., osteoarthritis) according to an embodiment of the devices and methods described herein.

Described herein are devices and methods for treating DJD.

Induced time-varying currents from PEMF or PRF devices may be configured to effect joint tissue including specific molecular pathways in the target tissue allowing these tissues to react in a physiologically meaningful manner. For example, a waveform may be configured within a prescribed set of parameters so that a particular pathway, such as CaM-dependent NO synthesis within the tissue target, is modulated specifically. Both the applied waveform and the dosing or treatment regime applied may be configured so that this pathway is targeted specifically and effectively. Further, the stimulation protocol and dosing regime may be configured so that the device (applicator device) may be portable/wearable and lightweight, and operate at a clinically significant level yet require low power.

For example, the electrical properties of a joint and affected tissue target structure may be included in the calculation, affecting the levels and distributions of induced current. Molecules, cells, tissue, and organs are all in an induced current pathway such as cells in a gap junction contact may be modeled as equivalent electrical structures, and the applied electromagnetic signal may be tested against this model to tune the applied signal to the desired response. Ion or ligand interactions at binding sites on macromolecules that may reside on a membrane surface are voltage dependent chemical processes (e.g., electrochemical process) that can respond to an induced electromagnetic field ("E") in this model. Induced current may arrive at these sites via a surrounding ionic medium. The presence of cells in a current pathway causes an induced current ("J") to decay more rapidly with time ("J(t)"). This is due to an added electrical impedance of cells from membrane capacitance and ion binding time constants of binding and other voltage sensitive membrane processes such as membrane transport. Ion binding time constants may be used to determine the optimal stimulation parameters and to determine the appropriate SNR or PSNR to be evaluated for any proposed EMF signal configuration. Preferably ion binding time constants in the range of about 0.1 to about 100 msec are used in the model.

Equivalent electrical circuit models representing various membrane and charged interface configurations have been derived. For example, in Calcium ("$Ca^{2+}$") binding, the change in concentration of bound $Ca^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where $\omega$ is angular frequency defined as $2\pi f$, where f is frequency, $i = -1^{1/2}$, $Z_b(\omega)$ is the binding impedance, and $R_{ion}$ and $C_{ion}$ are equivalent binding resistance and capacitance of an ion binding pathway. The value of the equivalent binding time constant, $\tau_{ion} = R_{ion}C_{ion}$, is related to an ion binding rate constant, $k_b$, via $\tau_{ion} = R_{ion}C_{ion} = 1/k_b$. Thus, the characteristic time constant of this pathway is determined by ion binding kinetics.

Induced E from a PEMF or PRF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to a surface concentration of $Ca^{2+}$ ions in the binding site that is storage of charge is equivalent to storage of ions or other charged species on cell surfaces and junctions. Electrical impedance measurements, as well as direct kinetic analyses of binding rate constants, provide values for time constants necessary for configuration of a PEMF waveform to match a bandpass of target (e.g., joint) structures. This allows for a required range of frequencies for any given induced E waveform for optimal coupling to target impedance, such as bandpass.

Ion binding which activates, e.g., regulatory enzymes constitutes an EMF target pathway, for example Ca binding to CaM. Use of this pathway is based upon acceleration of tissue repair, for example bone repair, wound repair, joint and affected tissue repair, and repair of other molecules, cells, tissues, and organs that involves modulation of cytokines and growth factors released in various stages of tissue repair and maintenance. Growth factors such as platelet derived growth factor ("PDGF"), basic fibroblast growth factor ("FGF-2"), vascular endothelial growth factor ("VEGF") and epidermal growth factor ("EGF") are all involved at an appropriate stage of healing. Angiogenesis and neovascularization are also integral to tissue growth and repair and can be modulated by PEMF. All of these factors are CaM-dependent.

Utilizing a Ca/CaM pathway a waveform can be configured for which induced power is sufficiently above background thermal noise power. Under correct physiological conditions, this waveform can have a physiologically significant bioeffect.

Application of a SNR or PSNR model to Ca/CaM requires knowledge of electrical equivalents of $Ca^{2+}$ binding kinetics at CaM. Within first order binding kinetics, changes in concentration of bound $Ca^{2+}$ at CaM binding sites over time may be characterized in a frequency domain by an equivalent binding time constant, $\tau_{ion} = R_{ion}C_{ion}$, where $R_{ion}$ and $C_{ion}$ are equivalent binding resistance and capacitance of the ion binding pathway, $\tau_{ion}$ is related to a ion binding rate constant, $k_b$, via $\tau_{ion}=R_{ion}C_{ion}=1/k_b$. Published values for $k_b$ can then be employed in a cell array or single cell model to evaluate SNR by comparing voltage induced by a PRF signal to thermal fluctuations in voltage at a CaM binding site. Employing numerical values for PMF response, such as $V_{max}=6.5\times10^{-7}$ sec$^{-1}$, [Ca$^{2+}$]=2.5 μM, KD=30μM, [Ca$^{2+}$CaM]=KD([Ca$^{2+}$]+ [CaM]), yields $k_b$=665 sec$^{-1}$ ($\tau_{ion}$=1.5 msec). Such a value for $\tau_{ion}$ can be employed in an electrical equivalent circuit for ion binding while SNR or PSNR analysis can be performed for any waveform structure.

According to one embodiment, a mathematical model can be configured to assimilate that thermal noise which is present in all voltage dependent processes and represents a minimum threshold requirement to establish adequate SNR or PSNR. Power spectral density, $S_n(\omega)$, of thermal noise can be expressed as:

$$S_n(\omega)=4kTRe[Z_M(x,\omega)]$$

where $Z_M(x,\omega)$ is electrical impedance of a target pathway structure (e.g., joint tissue), x is a dimension of a joint tissue structure and Re denotes a real part of impedance of a the target pathway tissue structure. $Z_M(x,\omega)$ can be expressed as:

$$Z_M(x,\omega) = \left[\frac{R_e + R_i + R_g}{\gamma}\right]\tanh(\gamma x)$$

This equation shows that electrical impedance of the target pathway (including the target tissue), and contributions from extracellular fluid resistance ("$R_e$"), intracellular fluid resistance ("$R_f$") and intermembrane resistance ("$R_g$") which are electrically connected to target pathway structures and, all contribute to noise filtering.

A typical approach to evaluation of SNR uses a single value of a root mean square (RMS) noise voltage. This is calculated by taking a square root of an integration of $S_n(\omega)$=4kT Re[$Z_M$(x,$\omega$)] over all frequencies relevant to either a complete membrane response, or to bandwidth of a target structure. SNR can be expressed by a ratio:

$$SNR = \frac{|V_M(\omega)|}{RMS}$$

where $|V_M(\omega)|$ is maximum amplitude of voltage at each frequency as delivered by a chosen waveform to the joint tissue.

In one embodiment, a burst of sinusoidal waves, having a frequency between about 1 MHz and 50 MHz, is applied to the joint or affected tissue so that the effect of therapy upon the relevant dielectric pathways, such as, cellular membrane receptors, ion binding to macromolecules and general transmembrane potential changes, is modulated. According y, by increasing a number of frequency components transmitted to relevant cellular pathways, a large range of biophysical phenomena, such as modulating growth factor and cytokine release and ion binding at regulatory molecules, applicable to known tissue growth and repair mechanisms are accessible. According to one embodiment, applying a random, or other high spectral density envelope, to a pulse burst envelope of mono-polar or bi-polar rectangular or sinusoidal pulses inducing peak electric fields between about $10^{-8}$ and about 100 MV/cm, produces an effect on biological healing processes applicable to both soft and hard tissues.

One embodiment of the methods and devices described herein comprises an electromagnetic signal having a pulse burst envelope of spectral density to efficiently couple to physiologically relevant dielectric pathways, such as cellular membrane receptors, ion binding to macromolecules, and general transmembrane potential changes. The use of a burst duration which is generally below 100 microseconds for each burst, limits the frequency components that could couple to the relevant dielectric pathways in cells and tissue, and have marginal or no bioeffect unless excessive and non-selective amplitudes are delivered to the target. In one embodiment, the waveform comprises an increased number of frequency components transmitted to relevant cellular pathways whereby access to a larger range of biophysical phenomena applicable to known healing mechanisms, including enhanced second messenger release, enzyme activity and growth factor and cytokine release can be achieved. By increasing burst duration and applying a random, or other envelope, to the pulse burst envelope of mono-polar or bi-polar rectangular or sinusoidal pulses which induce peak electric fields between $10^{-8}$ and 100 mV/cm, a more efficient and greater effect can be achieved on biological healing processes applicable to both soft and hard tissues in humans, animals and plants.

The present invention teaches that a time-varying electromagnetic field for which pulse duration or carrier period is less than about half of the bound ion lifetime of Ca$^{2+}$ binding to CaM will maximize the current flow into the Ca/CaM binding pathway to accelerate the CaM-dependent signaling which plants, animals and humans utilize for tissue growth, repair and maintenance. In particular, a time-varying electromagnetic field may be configured to modulate CaM-dependent NO/cGMP signaling which accelerates; pain and edema relief, angiogenesis, hard and soft tissue repair, repair of ischemic tissue, prevention and repair of neurodegenerative diseases, nerve repair and regeneration, skeletal and cardiac muscle repair and regeneration, relief of muscle pain, relief of nerve pain, relief of angina, relief of degenerative joint disease pain, healing of degenerative joint disease, immunological response to disease, including cancer.

A preferred embodiment according to the present invention is an electromagnetic signal which accelerates the kinetics of Ca$^{2+}$ binding by maximizing non-thermal $E_b$(s) at its CaM binding sites, consisting of a 1-10 msec pulse burst of 27.12 MHz radio frequency sinusoidal waves, repeating between about 1 and about 5 bursts/sec and inducing a peak electric field between about 1 and about 100 V/m, then coupling the configured waveform using a generating device such as ultra lightweight wire coils that are powered by a waveform configuration device such as miniaturized electronic circuitry which is programmed to apply the waveform at fixed or variable intervals, for example 1 minute every 10 minutes, 10 minutes every hour, or any other regimen found to be beneficial for a prescribed treatment.

According to the present invention, the application of non-thermal EMF instantaneously accelerates the kinetics of Ca$^{2+}$ binding to CaM, the first step of a well characterized signaling cascade which a plant, animal or human organism utilizes to respond to chemical or physical insults. Ca/CaM binding is kinetically asymmetrical, i.e., the rate of binding exceeds the rate of dissociation by several orders of magnitude ($k_{on} \gg k_{off}$), therefore the application of EMF will instantaneously drive the reaction in the forward direction. The Ca/CaM binding time constant is in the range of 1 to 10 milliseconds. In contrast, the release of Ca$^{2+}$ from CaM cannot occur until cNOS* has converted L-arginine to citrulline and NO, which takes the better part of a second. Subsequent reactions involving NO depend upon the cell/tissue state. For example, tissue repair requires a temporal sequence of inflammatory, anti-inflammatory, angiogenic and proliferative components. Endothelial cells orchestrate the production of FGF-2 and VEGF for angiogenesis. For each of these phases, early NO production by endothelial cells, leading to increased cGMP by these, as well as other NO targets, such as vascular smooth muscle, are modulated by an EMF effect on GC via Ca/CaM binding. In contrast, nerve or bone regeneration require other pathways leading to differentiation during development and growth, and prevention of apoptosis, as in response to injury or neurodegenerative diseases. For these cases, early cAMP formation is modulated by an EMF effect on AC via Ca/CaM binding.

Another embodiment comprises known cellular responses to weak external stimuli such as heat, light, sound, ultrasound and electromagnetic fields. For cells in homeostasis, i.e., no injury, responses to such stimuli, if configured to modulate CaM-dependent signaling can be the production of protective proteins, for example, heat shock proteins, which enhance the ability of the cell, tissue, organ to withstand and respond to external stimuli which further disrupt homeostasis, Electromagnetic fields configured according to one embodiment modulate the release of such compounds by modulating CaM-dependent NO signaling thus advantageously providing an improved means to enhance prophylactic protection and wellness of living organisms from diseases such as DJD.

The methods and devices described herein may relate to therapeutically beneficial methods and apparatus for non-invasive pulsed electromagnetic treatment for enhanced condition, repair and growth of living tissue in animals, humans and plants, This beneficial method operates to selectively change the bioelectromagnetic environment associated with specific pathways within the cellular and tissue environment through the use of electromagnetic means such as PRF generators and applicator heads. More particularly use of electromagnetic means may include the provision of a flux path to a selectable body region, of a succession of PEMF pulses having a minimum width characteristic of at least 0.01 microseconds in a pulse burst envelope having between 1 and 100,000 pulses per burst, in which a voltage amplitude envelope of said pulse burst is defined by a randomly varying parameter. Further, the repetition rate of such pulse bursts may vary from 0.01 to 10,000 Hz. Additionally a mathematically-definable parameter can he employed in lieu of said random amplitude envelope of the pulse bursts.

According to one embodiment, by applying a random, or other high spectral density envelope, to a pulse burst envelope of mono-polar or hi-polar rectangular or sinusoidal pulses which induce peak electric fields between $10^{-8}$ and $100$ mV/cm, a more efficient and greater effect can be achieved on biological healing processes applicable to both soft and hard tissues in humans, animals and plants. A pulse burst containing high frequency waveforms can advantageously and efficiently couple to physiologically relevant dielectric pathways, such as, cellular membrane receptors, ion binding to cellular enzymes, and general transmembrane potential changes thereby modulating angiogenesis and neovascularization.

In some variations, the methods and/or device may utilize a SNR or a PSNR approach to configure bioeffective waveforms in the Ca/CaM target pathway and incorporates miniaturized circuitry and lightweight flexible coils. This advantageously allows a device that utilizes a SNR or PSNR approach in the Ca/CaM target pathway, miniaturized circuitry, and lightweight flexible coils, to be completely portable and if desired to be constructed as disposable and if further desired to be constructed as implantable. The lightweight flexible coils can be an integral portion of a positioning device such as surgical dressings, wound dressings, pads, seat cushions, mattress pads, wheelchairs, chairs, and any other garment and structure juxtaposed to living tissue and cells for co-treatment or co-maintenance thereof. By advantageously integrating a coil into a positioning device therapeutic treatment can be provided to living tissue and cells in an inconspicuous and convenient manner.

Specifically, broad spectral density bursts of electromagnetic waveforms, configured to achieve optimum signal amplitude within a bandpass of a biological target, are selectively applied to affected tissue to treat DJD. Waveforms may be selected using the amplitude/power comparison with that of thermal noise in a target structure. Signals may comprise bursts of at least one of sinusoidal, rectangular, chaotic and random wave shapes, have frequency content in a range of 0,01 Hz to 100 MHz at 1 to 100,000 bursts per second, have a burst duration from 0.01 to 100 milliseconds, and a burst repetition rate from 0.01 to 1000 bursts/second. Peak signal amplitude at the target structure may fall in a range of 1 microvolt percentimeter ("µV/cm") to 100 mV/cm. Each signal burst envelope may be a random function providing a means to accommodate different electromagnetic characteristics of healing tissue, The signal may comprise a 20 millisecond pulse burst, repeating at 1 to 10 bursts/second and comprising 0.1 to 200 microsecond symmetrical or asymmetrical pulses repeating at $10^{-5}$ to 100 kilohertz within the burst. The burst envelope can be modified 1/f function or any arbitrary function and can be applied at random repetition rates. Fixed repetition rates can also be used between about 0.1 Hz and about 1000 Hz. An induced electric field from about $10^{-8}$ mV/cm to about 100 mV/cm is generated. Another embodiment comprises a 4 millisecond burst of high frequency sinusoidal waves, such as 27.12 MHz, repeating at 1 to 100 bursts per second. An induced electric field from about $10^{-8}$ mV/cm to about 100 mV/cm is generated. Resulting waveforms can be delivered via inductive or capacitive coupling for 1 to 30 minutes treatment sessions delivered according to predefined regimes by which PEMF treatment may be applied for 1 to 50 daily sessions, repeated daily, The treatment regimens for any waveform configured according to an embodiment of the devices and methods described herein may be fully automated. The number of daily treatments may be programmed to vary on a daily basis according to any predefined protocol.

Applying a burst of high frequency waveforms significantly reduces the power requirements to inductively couple a PEMF signal configured according to an embodiment of the devices and methods described herein. This is because the rate of change of the magnetic field ("dB/dt") of a high frequency waveform is substantially greater than that of a low frequency waveform, allowing the required amplitude/power to be applied to target pathways in affected tissue with significantly less power. In addition, a high frequency waveform can be more easily configured to modulate the target pathway. Accordingly, the dual advantages, of selective transmitted dosimetry to the relevant dielectric pathways and of decreased power requirement may be achieved.

FIG. 1 is a flow diagram of a method for treating a subject for DJD. Before beginning the method of treatment, one or more (or a range of) waveforms may be determined that target the appropriate pathway (e.g. the Ca/CaM pathway) in the target tissue. Method of determining appropriate waveforms are described herein, and exemplary waveforms, as well as a range of values (e.g., on-time/off-time, frequency, power, etc.) are provided herein for treatment of DJD.

As described in FIG. 1, a method of treating DJD may include the step of placing the tissue to be treated (one or more joints) in contact with, or in proximity to, the PEMF device 101. Thus, the PEMF device may be coupled to a target tissue (e.g., joint). Any appropriate PEMF device may be used. In general, the PEMF device may be configured to apply electromagnetic energy of the appropriate power and waveform to selectively and specifically modulate the Ca/CaM pathway, as described herein. The PEMF device may include an applicator (e.g., an inductor applicator) which may placed adjacent to or in contact with the affected tissue, e.g., joint. The PEMF device may also include a signal conditioner/processor for forming the appropriate waveform. The stimulator may include a timing element (e.g., circuit, etc.) for controlling the timing automatically after the start of stimulation 103.

In the example shown in FIG. 1, once stimulation is begun 103, the PEMF device typically applies an envelope of high-frequency waveforms at low (e.g., less than 50 milliGauss, less than 100 milliGauss, less than 200 milliGauss, etc.) amplitude. The envelope of high-frequency pulses is then repeated at a particular frequency after an appropriate delay (e.g., at 2 Hz, 1 Hz, etc.). This series of bursts can be repeated for a first treatment time (e.g., 5 minutes, 15 minutes, 20 minutes, 30 minutes) and then followed by a delay during which the stimulation is "off" 107. This waiting interval (inter-treatment interval) may last for minutes or hours (e.g., 15 minutes, 2 hours, 4 hours, 8 hours, 12 hours, etc.), and then the stimulation interval can be repeated again until the treatment regime is complete 109.

In some variations, the stimulation device is pre-programmed (or configured to receive pre-programming) to execute the entire treatment regime (including multiple on-periods (intra-treatment intervals) punctuated by predetermined off-periods (inter-treatment intervals) when no stimulation is applied.

As mentioned, in general, a generated electromagnetic signal may be comprised of a burst of arbitrary waveforms having at least one waveform parameter that includes a plurality of frequency components ranging from about 0.01 Hz to about 100 MHz wherein the plurality of frequency components satisfies a SNR or PSNR model in respect to an ion binding pathway. A repetitive electromagnetic signal can be generated, for example inductively or capacitively, from the configured at least one waveform. The electromagnetic signal may be coupled to the affected tissue structure so that a target pathway (e.g., molecular pathway of ions and ligand binding) is effected by the output of the coupling element (such as an electrode or an inductor) placed in close proximity to the target structure. The coupling may modulate binding of target ions and ligands to regulatory molecules, tissues, cells, and organs (e.g., the activity of the Ca/CaM pathway and the production of NO). In one variation, PEMF signals configured using SNR or PSNR analysis match the bandpass of a second messenger, e.g., $Ca^{2+}$ whereby the PEMF signals can act as a first messenger to modulate biochemical cascades such as production or inhibition or up or down-regulation of cytokines, Nitric Oxide, Nitric Oxide Synthase and growth factors that are related to tissue growth and repair. A detectible E field amplitude is produced within a frequency response of $Ca^{2+}$ binding to CaM.

Figure 2:
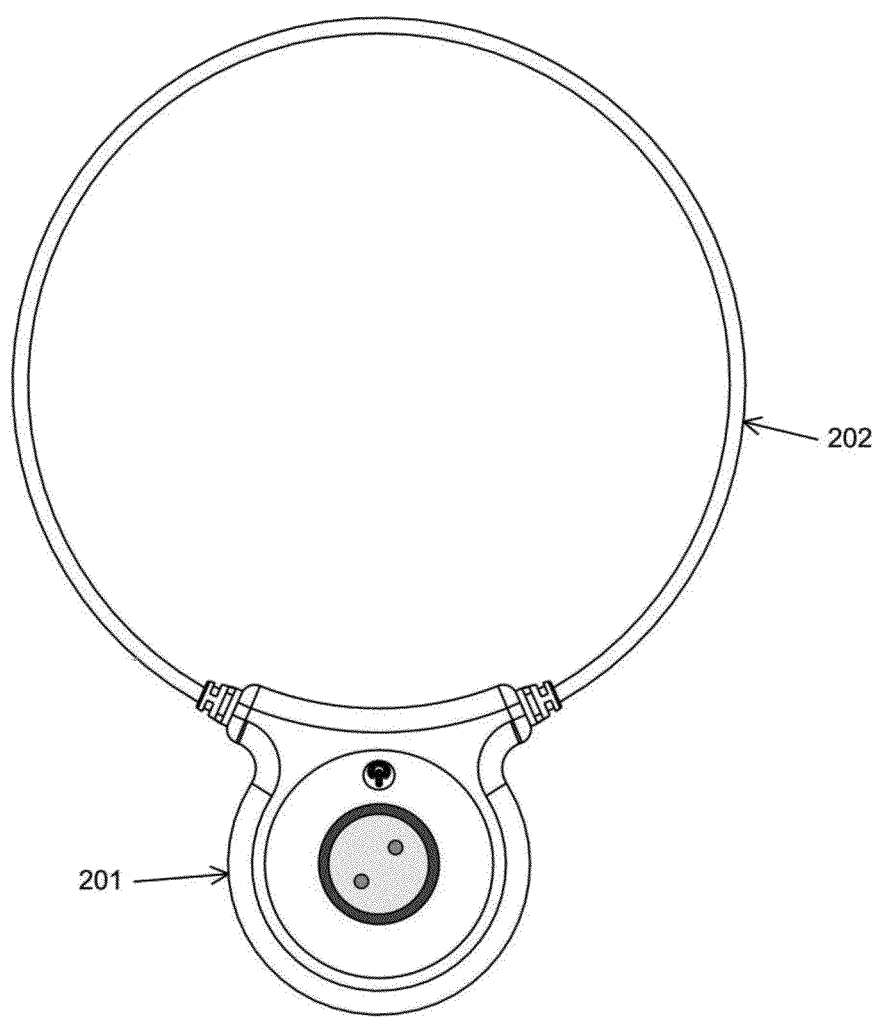
FIG. 2 is a view of an apparatus for application of electromagnetic signals according to an embodiment of the devices and methods described herein.

FIG. 2 illustrates an embodiment of an apparatus that may be used. The apparatus is constructed to be self-contained, lightweight, and portable. A miniature control circuit 201 may be held within a (wearable) housing and connected to a generating device such as an electrical coil 202. The miniature control circuit 201 is constructed in a manner that applies a mathematical model, the results of a mathematical model, or that otherwise incorporates the asymmetrical kinetics of ion binding to intracellular buffers to configure electromagnetic waveforms to increase the rate of ion binding and enhance the biochemical signaling pathways living systems employ for growth, repair and maintenance. The configured waveforms may satisfy a SNR or a. PSNR model, or the asymmetrical kinetics of intracellular ion binding to a buffer, so that for a given and known target pathway within a joint (e.g., the Ca/CaM pathway), it is possible to choose waveform parameters that satisfy a frequency response of the target pathway within the target tissue and SNR or PSNR of at least about 0.2 to modulate ion and/or ligand interactions whereby the ion and/or ligand interactions are detectable in the target tissue pathway above baseline thermal fluctuations in voltage, wherein SNR or PSNR is evaluated by calculating a frequency response of the impedance of the target path structure divided by the RMS of baseline thermal fluctuations in voltage across the target path structure. A mathematical model to induce a time-varying magnetic field and a time-varying electric field in a target tissue (e.g., joint and surrounding affected tissue) may be used to determine the waveform(s) that effect a specific molecular pathway such as the Ca/CaM pathway; for example a waveform may include about. 0.001 to about 100 msec bursts of about 1 to about 100 microsecond rectangular pulses, having a burst duration of about 0.01 to 100,000 microseconds and repeating at about 0.1 to about 100 pulses per second. Peak amplitude of the induced electric field is between about 1 uV//cm and about 100 mV/cm, that can be constant or varied according to a mathematical function, for example a modified 1/f function where f=frequency. A waveform configured as described herein may be applied to a joint (e.g., knee, hip, elbow, shoulder, wrist, ankle, etc.), preferably for a total exposure time of under 1 minute to 240 minutes daily. However other exposure times can be used. Waveforms configured by the miniature control circuit 201 are directed to a generating device 202 such as electrical coils. Preferably, the generating device 202 is a conformable coil for example pliable, comprising one or more turns of electrically conducting wire in a generally circular or oval shape however other shapes can be used. The generating device 202 delivers a pulsing magnetic field configured according to a mathematical model that can be used to provide treatment of DK). The miniature control circuit may apply a pulsing magnetic field for a prescribed time and can automatically repeat applying the pulsing magnetic field for as many applications as are needed in a given time period, for example 12 times a day. The miniature control circuit can be configured to be programmable applying pulsing magnetic fields for any time repetition sequence. In one variation, the devices described herein can be positioned to treat one or more joints by being incorporated with a positioning device such as a bandage, a dressing, a vest, a brassiere, or an anatomical support thereby making the unit self-contained. Coupling a pulsing magnetic field to the target tissue may reduce existing inflammation thereby reducing pain and promoting healing in treatment areas. Coupling a pulsing magnetic field to healthy target tissue may prevent inflammation and subsequent joint destruction by modulation of CaM-dependent HSP resease. When electrical coils are used as the generating device 202, the electrical coils can be powered with a time varying magnetic field that induces a time varying electric field in a target joint according to Faraday's law. An electromagnetic signal generated by the generating device 202 can also be applied using electrochemical coupling, wherein electrodes are in direct contact with skin or another outer electrically conductive boundary of joint. Yet in another embodiment, the electromagnetic signal generated by the generating device 202 can also be applied using electrostatic coupling wherein an air gap exists between a generating device 202 such as an electrode and the target tissue. An advantage of the devices described herein is that the ultra lightweight coils and miniaturized circuitry allow for use with common physical therapy treatment modalities, and at any location for which tissue growth, pain relief, and tissue and organ healing is desired. An advantageous result of application of the devices and methods described herein is that tissue growth, repair, and maintenance can be accomplished and enhanced anywhere and at anytime. Yet another advantageous result of application as described. herein is that growth, repair, and maintenance of molecules, cells, tissues, and organs can be accomplished and enhanced anywhere and at anytime. Another embodiment delivers PEMF to treat DJD, regardless of the actual mechanism of action.

The electrical coil may be referred to as a coil applicator, a flexible coil, a coil wire applicator, or the like, in some variation, the coil is a wire applicator that has a diameter (When circular) of approximately 6 inches, 7 inches, 8 inches, etc. In general, the size of the coil may be fixed, and the control circuit may be matched to the material and size of the applicator to provide the desired stimulation.

Figure 3:
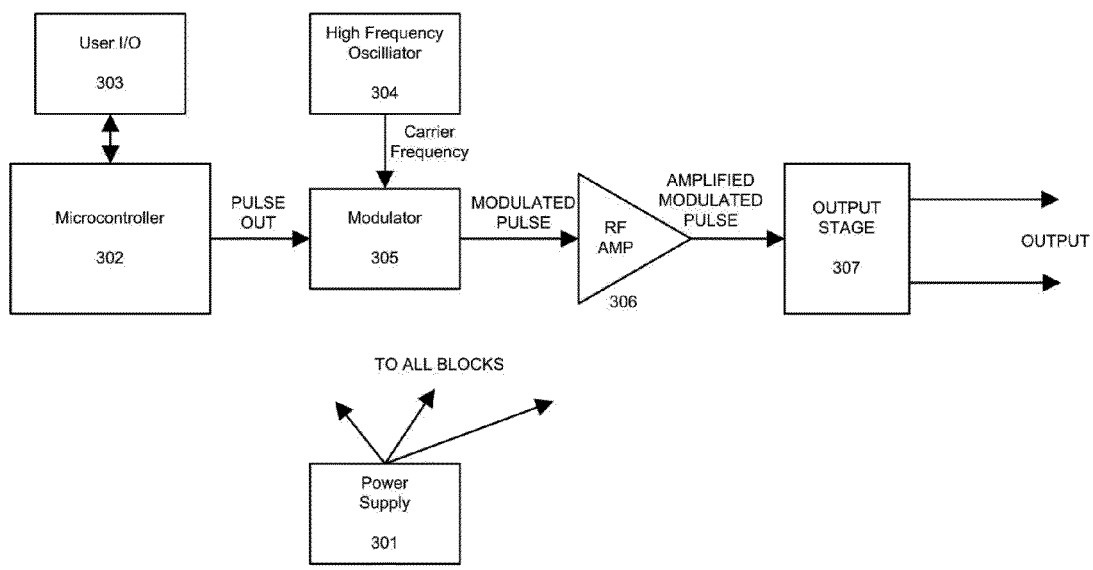
FIG. 3 is a block diagram of miniaturized circuitry according to an embodiment of the devices and methods described herein.

FIG. 3 depicts a block diagram of an embodiment of the devices described herein, comprising a miniature control circuit 300. The miniature control circuit 300 produces waveforms that drive a generating device such as wire coils described above in FIG. 2. The miniature control circuit can be activated by any activation means such as an on/off switch 303. The miniature control circuit 300 has a power source 301. Preferably the power source has an output voltage of 3.3 V but other voltages can be used. In another embodiment, the power source can be an external power source such as an electric current outlet such as an AC/DC outlet, coupled to the device, for example by a plug and wire. The micro-controller 302 uses an 8 bit 4 MHz microprocessor but other bit/MHz combination microprocessors may be used. The micro-controller 302 also controls a pulse modulator 305. The pulse modulator 305 determines pulse shape, burst width, burst envelope shape, and burst repetition rate. In one embodiment, the pulse modulator 305 produces waveforms that are configured to be detectable above background electrical activity at a target structure e.g., at the target Ca/CaM pathway in the target tissue) by satisfying a SNR and/or PSNR mathematical model. An integral high frequency oscillator 304, such as a sine wave or arbitrary number generator, can also be incorporated to provide specific waveforms. A radio frequency amplifier 306 increases the amplitude of the modulated pulse prior to the output stage 307. The output stage 307 delivers the amplified waveform to at least one coupling device such as an inductor. The micro-controller 302 can also control total exposure time of a single treatment. The miniature control circuit 300 can be constructed to be programmable and apply a pulsing electromagnetic field for a prescribed time and to automatically repeat applying the pulsing electromagnetic field for as many applications as are needed in a given time period, for example 10 times a day. Preferably treatments times of about 1 minute to about 30 minutes are used.

Figure 4:
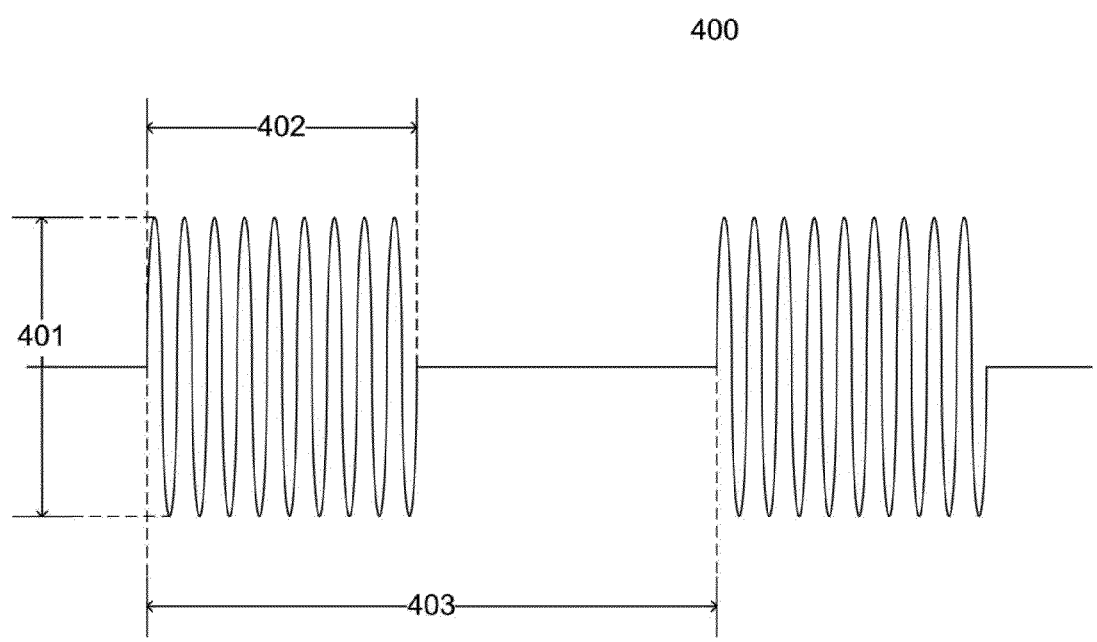
FIG. 4 depicts features of a waveform that may be delivered as described herein.

Referring to FIG. 4, one variation of a waveform 400 is illustrated. A high frequency sinusoid of amplitude 401 is repeated within a burst 402 that has a finite duration, alternatively referred to as width. The duration 402 is such that a duty cycle which can be defined as a ratio of burst duration to signal period 403 is between about 1 to about $10^{-5}$. A sinusoidal waveform having a frequency in the 1-100 MHz range may be utilized, but any waveform with any fixed or variable duration and any fixed or variable modulation, or any arbitrary waveform may be employed.

FIGS. 5A to 5D illustrate variations of the devices as described herein for the treatment of DJD in which the devices can be stand-alone or incorporated into one or more garments, braces, orthotics, or the like. As mentioned above, the devices (or systems) may include an applicator, a signal generation component and a power component. These components may be in a single, integrated unit, or they may be may be modular or separate (in any sub-combinations). The device of the various components may be embedded or integral with other products or elements.

Figure 5A:

For example, in the stand-alone PEMF device which delivers a signal configured according to an embodiment of the devices and methods described herein, shown in FIG. 5A, an applicator 501 and signal generation unit and power components are shown. A patient may place this unit in proximity to the affected tissue, e.g., knee joint, and manually start the treatment regime. This is the device utilized in the clinical study of Example 4. In FIG. 5B, the applicator portion 503 is attached to the brace to apply the PEMF signal to the affected tissue, while the other elements (e.g., the signal generation and power components) are shown housed within a removable and replaceable activation unit 513, connected by a wire (not visible). In another example shown in FIG. 5C, an integrated applicator can be adapter to fit directly on the affected area of the body and be used as a stand-alone unit, as needed. This example includes an applicator 507 and a separate activation unit 505, and is configured to be part of a hip brace. Similarly, FIG. 5D illustrates a variation configure to be part of a belt or girdle structure which also includes an applicator 509 and may include a separate activation unit 511. In the hip, the brace could have the same independent, modular components, and in the back as well.

Other potential forms include full modular systems in which a "family" of braces embeds (visibly or completely integrated) applicator and specific system components and the signal generator is completely interchangeable with all the anatomical applicators.

Figure 6:
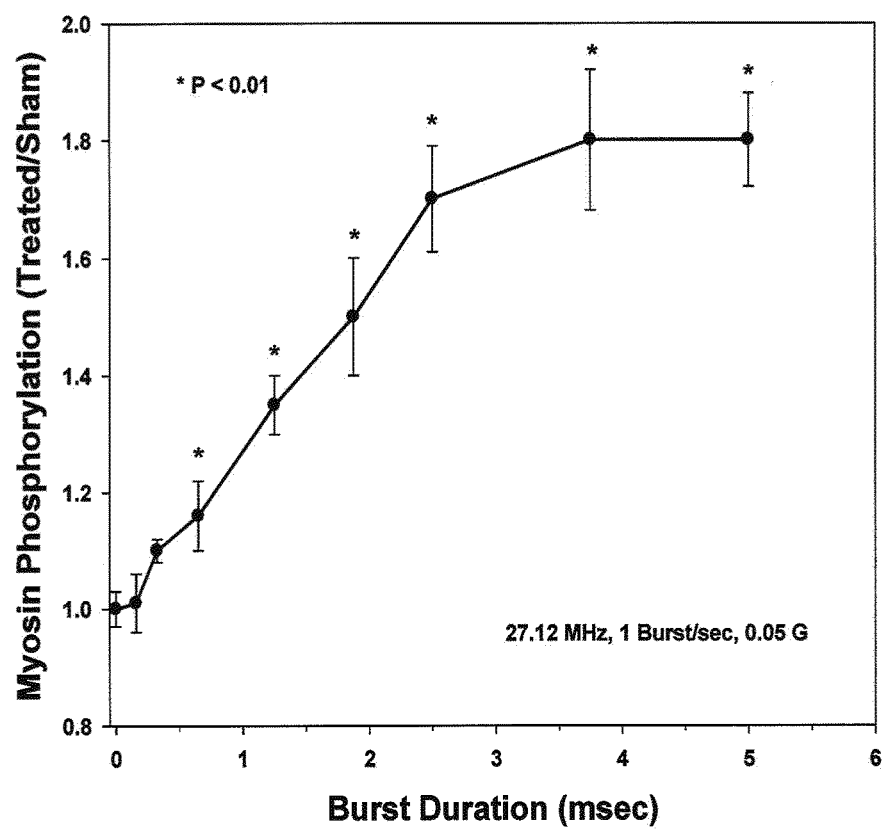
FIG. 6 is a curve illustrating the effect of burst duration on myosin phosphorylation for an EMF signal configured according to an embodiment of the devices and methods described herein.

FIG. 6 is a plot describing the experimental results of the study given in EXAMPLE 1. A pulse modulated radio frequency signal, configured to modulate CaM-dependent enzyme kinetics as described herein, accelerated myosin phosphorylation as a function of burst duration. The SNR and PSNR mathematical models predicted that significant increases in phosphorylation would be observed for burst durations of between 1 and 5 milliseconds at an amplitude of 50 mG. The plot shows that maximum acceleration of phosphorylation occurred at about 4 msec, with statistically significant increases starting at about 1 msec.

Figure 7:
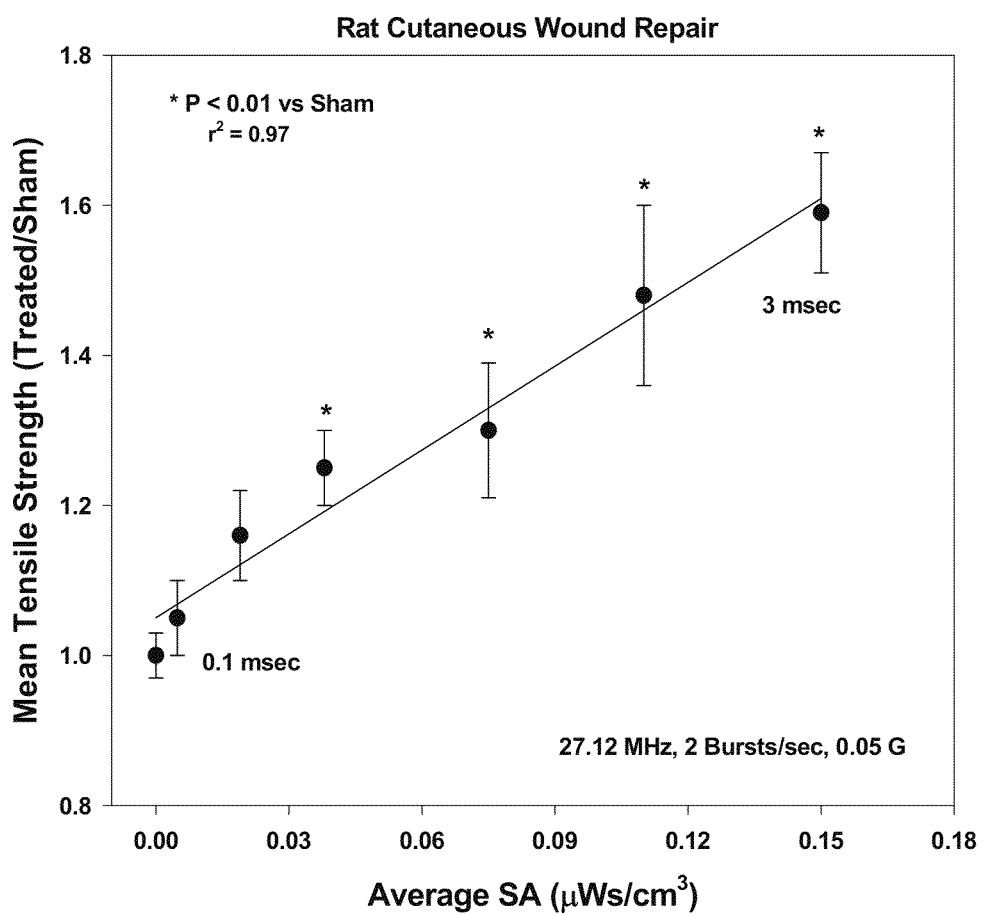
FIG. 7 is a curve illustrating the effect of burst duration of PEMF, configured according to one variation of the devices and methods described herein, on cutaneous wound repair in a rat model.

FIG. 7 is a plot describing the experimental results of the study given in EXAMPLE 2. A pulse modulated radio frequency signal, configured to modulate CaM-dependent NO signaling as described herein, was applied to a cutaneous wound healing model in the rat. The effect of burst duration was examined, The SNR and PSNR mathematical models predicted that significant acceleration of wound repair as measured by maximum tensile strength for burst durations of between 1 and 5 milliseconds at an amplitude of 50 mG, with no significant increases at smaller burst durations. The results, which are given in terms of PSNR (in units of specific absorption, SA), show that healing is a linear function of burst duration, with statistical significance starting at about 1 msec, in accord with the devices and methods described herein.

Figure 8A:
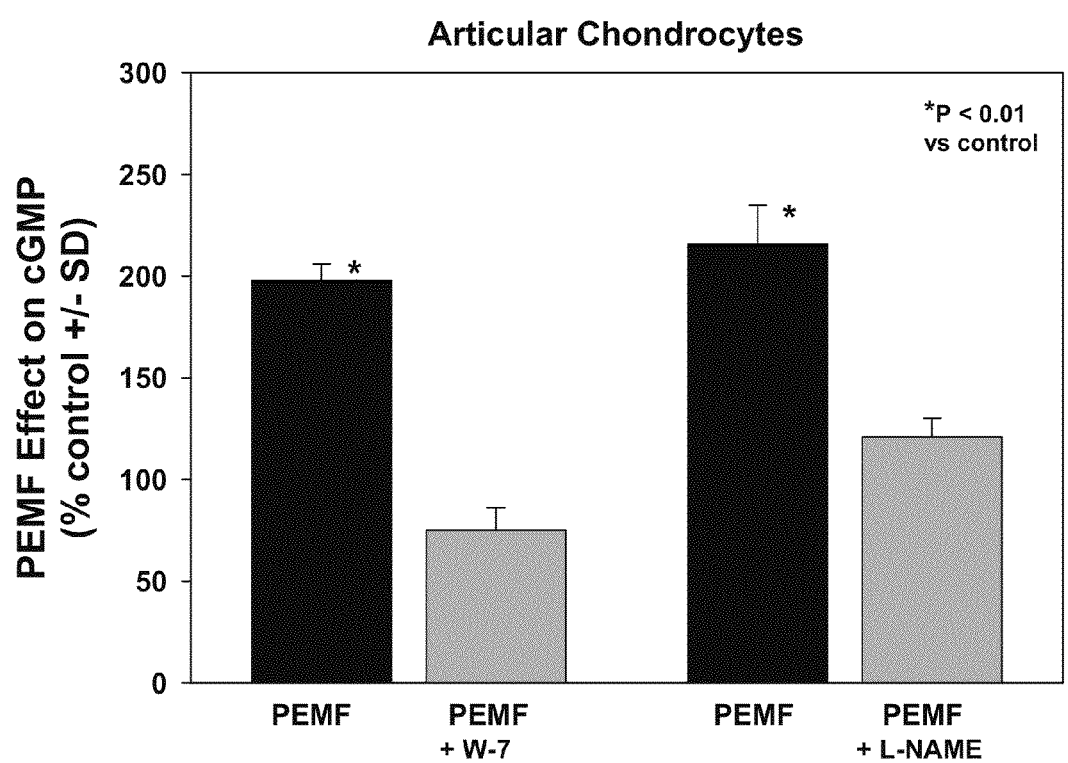
FIGS. 8A-B illustrate the effect of PEMF, configured according to one embodiment. of the devices and methods described herein, on articular chondrocyte proliferation through the use of inhibitors of early signaling pathways.
Figure 8B:
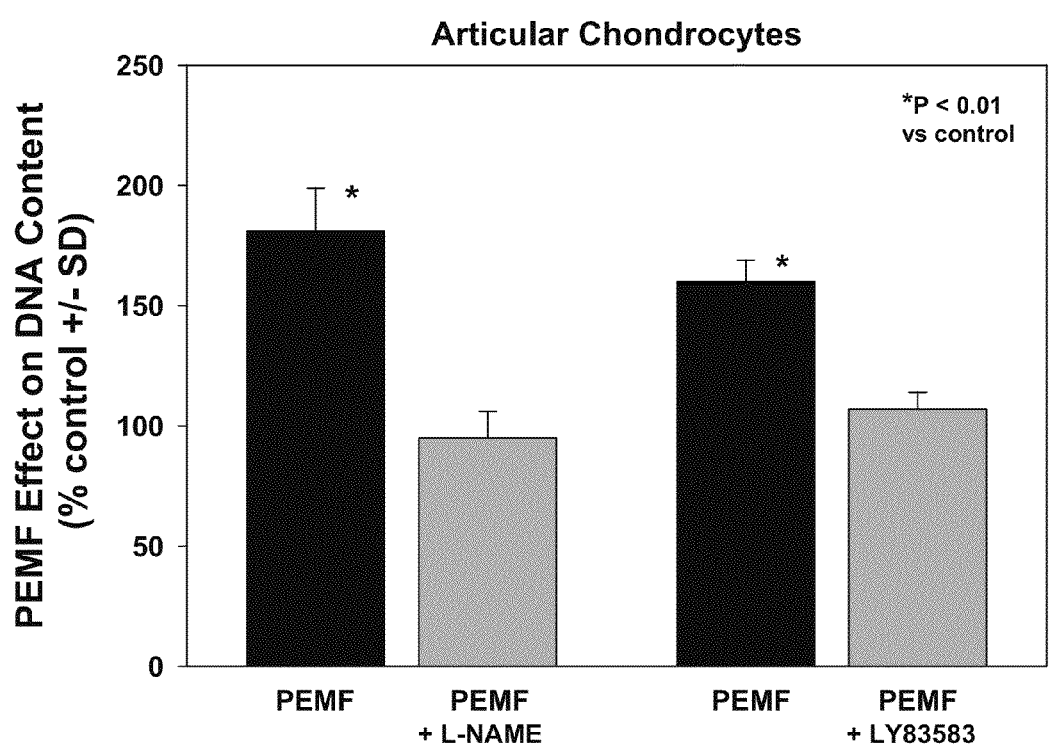

FIGS. 8A-B are bar graphs describing the experimental results of the study given in EXAMPLE 3. A PEMF signal, configured to modulate CaM-dependent NO signaling as described above, was applied to human cartilage cells in culture dishes to accelerate proliferation. After one 30 minutes PEMF treatment FIG. 8A shows that cGMP production was significantly increased at 30 minutes vs control cultures. This experiment incorporated the use of W-7, a CaM antagonist which blocks activated CaM from binding to and activating cNOS, and thereby annihilated the effect of PEMF on cGMP by preventing its effect on NO release, This experiment also incorporated the use of L-NAME a general cNOS inhibitor which also annihilated the effect of PEMF on cGMP release. These results indicate that this waveform, configured according to an embodiment of the devices and methods described herein, modulates CaM-dependent NO signaling, as measured by cGMP release.

FIG. 8B shows that cartilage cells receiving one 30 minute treatment with a signal configured to modulate CaM-dependent NO signaling produced a significant increase in DNA synthesis vs control cultures. Use of the cNOS inhibitor, L-NAME and the soluble guyanylyl cyclase inhibitor, LY83583, annihilated the PEMF effect on DNA synthesis. These results indicate that this waveform, configured according to an embodiment of the devices and methods described herein, modulates CaM-dependent NO signaling for DNA synthesis.

Figure 9:
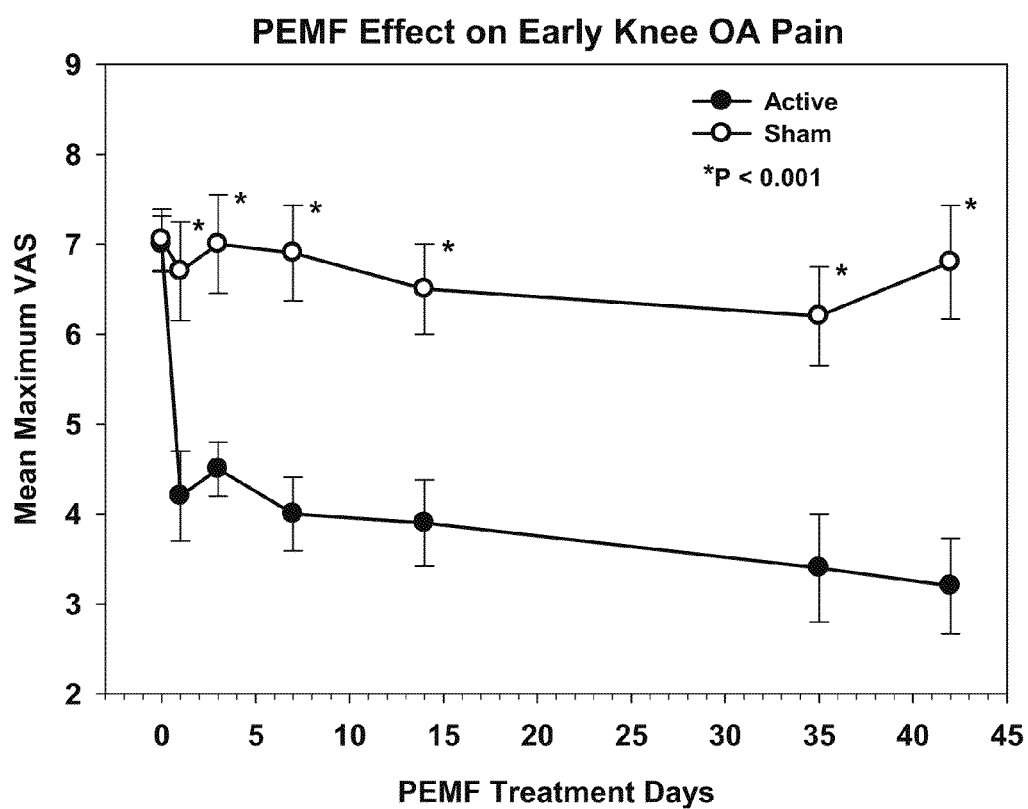
FIG. 9 illustrates the clinical effect of PEMF, configured according to an embodiment of the devices and methods described herein, on pain from osteoarthritis of the knee, in a randomized, double-blind, placebo-controlled human clinical trial.

FIG. 9 is a plot describing the results of a randomized double-blind clinical study on the effect of a PEMF signal, configured to modulate CaM-dependent NO signaling as described herein, significantly reduced pain from osteoarthritis of the knee. Patients in this study received the stand alone portable PEMF device shown in FIG. 5A, which delivered a 7 msec burst of 6.8 MHz sinusoidal waves repeating at 1/sec with 0.05 G peak amplitude, to the affected knee for 15 minutes twice daily, or as needed for pain relief. The results show PEMF caused a significant decrease in mean maximum pain, measured using a visual analogue scale, VAS, to approximately 45% of mean start VAS for the treated group by the end of day 1, which gradually fell to 55% of mean start VAS (P<0.001). In contrast, there was no significant decrease in mean maximum VAS vs mean start VAS at any time point in the sham group (P=0.555). There was no significant difference in mean start VAS between the active and sham groups (Active=7±0.31, Sham=7.1±0.34, P=0.903). It is believed these clinical results were obtained because the PEMF signal was able to be configured to modulate CaM-dependent signaling according to an embodiment of the devices and methods described herein.

It is further intended that any other embodiments of the devices and methods described herein that result from any changes in application or method of use or operation, method of manufacture, shape, size or material which are not specified within the detailed written description or illustrations and drawings contained herein, yet are considered apparent or obvious to one skilled in the art, are within the scope of the present invention.

EXAMPLE 1

The teachings for EMF signal configuration in the present invention have been tested experimentally on CaM-dependent myosin phosphorylation in a standard enzyme assay. The cell-free reaction mixture was chosen for phosphorylation rate to be linear in time for several minutes, and for sub-saturation free $Ca^{2+}$ concentration. This opens the biological window for Ca/CaM to be EMF-sensitive. This system is not responsive to PEMF if Ca is at saturation levels with respect to CaM, and reaction is not slowed to a minute time range, Experiments were performed using myosin light chain ("MIX") and myosin light chain kinase ("MLCK") isolated from turkey gizzard. A reaction mixture consisted of a basic solution containing 40 mM Hepes buffer, pH 7.0; 0.5 mM magnesium acetate; 1 mg/ml bovine serum albumin, 0.1% (w/) Tween80; and 1 mM EGTA12. Free $Ca^{2+}$ was varied in the 1-7 μM range. Once $Ca^{2+}$ buffering was established, freshly prepared 70 nM CaM, 160 nM MLC and 2 nM MLCK were added to the basic solution to form a final reaction mixture. The low MLC/MLCK ratio allowed linear time behavior in the minute time range. This provided reproducible enzyme activities and minimized pipetting time errors.

The reaction mixture was freshly prepared daily for each series of experiments and was aliquoted in 100 μL portions into 1.5 ml Eppendorf tubes. All Eppendorf tubes containing reaction mixture were kept at 0° C. then transferred to a specially designed water bath maintained at 37±0.1° C. by constant perfusion of water prewarmed by passage through a Fisher Scientific model 900 heat exchanger. Temperature was monitored with a thermistor probe such as a Cole-Parmer model 8110-20, immersed in one Eppendorf tube during all experiments. Reaction was initiated with 2.5 μM 32P ATP, and was stopped with Laemmli Sample Buffer solution containing 30 μM EDTA. A minimum of five blank samples were counted in each experiment. Blanks comprised a total assay mixture minus one of the active components $Ca^{2+}$, CaM, MLC or MLCK. Experiments for which blank counts were higher than 300 cpm were rejected. Phosphorylation was allowed to proceed for 5 minitures and was evaluated by counting 32P incorporated in MLC using a TM Analytic model 5303 Mark V liquid scintillation counter.

The signal comprised repetitive bursts of a high frequency waveform. Amplitude was maintained constant at 0.05 G and repetition rate was 1 burst/sec for all exposures. Burst duration varied from 65 μsec to 5000 μsec based upon projections of SNR and PSNR analyses which predicted that optional SNR and PSNR would be achieved as burst duration approached 1-2 msec. The results are shown in FIG. 6 wherein burst width 601 in msec is plotted on the x-axis and Myosin Phosphorylation 602 as treated/sham is plotted on the y-axis. It can be seen that the PEMF effect on $Ca^{2+}$ binding to CaM approaches its maximum at approximately 3 msec, in excellent agreement with the predictions of the SNR and PSNR model.

These results confirm that a PEMF signal, configured a priori as described above, would maximally increase myosin phosphorylation for burst durations sufficient to achieve optimal SNR and PSNR for a given magnetic field amplitude.

EXAMPLE 2

According to one variation, the teachings of the present invention in respect to CaM-dependent signaling allowed a priori configuration of PEMF signals to modulate cutaneous wound repair, A rat wound model has been well characterized both bio mechanically and biochemically, and was used in this study to examine the effect of modeled waveforms. Healthy, young adult male Sprague Dawley rats weighing approximately 300 grams were utilized.

The animals were anesthetized with an intraperitoneal dose of Ketamine 75 mg/kg and Medeto idine 0.5 mg/kg. After adequate anesthesia had been achieved, the dorsum was shaved, prepped with a dilute betadine/alcohol solution, and draped using sterile technique. Using a #10 scalpel, an 8-cm linear incision was performed through the skin down to the fascia on the dorsum of each rat. The wound edges were bluntly dissected to break any remaining dermal fibers, leaving an open wound approximately 4 cm in diameter. Hemostasis was obtained with applied pressure to avoid any damage to the skin edges. The skin edges were then closed with a 4-0 Ethilon running suture. Post-operatively, the animals received Buprenorphine 0.1-0.5 mg/kg, intraperitoneal. They were placed in individual cages and received food and water ad libitum.

PEMF exposure comprised pulsed radio frequency waveforms comprising a 100 usec to 3 msec burst of 27.12 MHz sinusoidal waves at 50 mG amplitude and repeating at 2 bursts/sec. PEMF was applied for 30 minutes twice daily.

Tensile strength was performed immediately after wound excision, Two 1 cm width strips of skin were transected perpendicular to the scar from each sample and used to measure the tensile strength in kg/mm$^2$. The strips were excised from the same area in each rat to assure consistency of measurement. The strips were then mounted on a tensiometer. The strips were loaded at 10 min/min and the maximum force generated before the wound pulled apart was recorded. The final tensile strength for comparison as determined by taking the average of the maximum load in kilograms per mm$^2$ of the two strips from the same wound, The results showed average ratio of treated/sham tensile strength was linearly dependent upon burst duration. PSNR analysis, a priori, predicted that the tensile strength of treated wounds would be significantly higher in the PEMF treated wounds only for burst durations of 1 msec and above, The results are given in FIG. 7, wherein the data is plotted using a PSNR analysis. Thus SA is specific absorption of PEMF signal energy in the Ca/CaM pathway. These results further confirm that a bioeffective signal may be configured on the basis of SNR or PSNR in the CaM-dependent NO signaling pathway according to an embodiment of the devices and methods described herein.

EXAMPLE 3

This example illustrates the effects of a PEMF signal configured to modulate CaM-dependent NO signaling in a culture of articular cartilage cells. A PEMF signal having a 5 msec burst of asymmetrical rectangular waves, applied for 30 minutes increased DNA synthesis in articular chondrocytes by 150% over 72 hours. That PEMF acted as a first messenger to modulate CaM-dependent. NO/cGMP signaling was confirmed by systematically using a CaM antagonist (W-7) to inhibit CaM activation of cNOS, Further support was obtained when L-nitrosoarginine methy ester (L-NAME), a cNOS inhibitor, and LY83583 a sGC inhibitor, to prevent the formation of cGMP, inhibited the increase in DNA. When either the CaM antagonist, or the NO, or the sGC inhibitor, was present during PEMF exposure, each one individually eliminated the PEMF effect on DNA synthesis at 72 hours, These results provide direct support that PEW acted as a first messenger to modulate CaM-dependent NO/cGMP signaling when the signal was configured according to an embodiment of the devices and methods described herein. A summary of these results showing abolition of the PEMF effect on cGMP at 15 minutes by W-7 and L-NAME is shown in FIG. 8A, and on DNA content at 72 hours by L-NAME and LY83583 in FIG. 8B.

EXAMPLE 4

This example illustrates the clinical effect of a PEMF signal, configured according to an embodiment of the devices and methods described herein to modulate CaM-dependent NO signaling, in a clinical study on pain from knee OA. This was a double-blind, randomized, placebo-controlled study of a total of 37 patients (19 active, 18 sham). Patient selection required an initial max visual analogue scale ("VAS") score >4, at least 2 hours of standing activity in a physical occupation, and no recent interventions such as cortisone injections or surgery. A PEMF signal, configured, a priori, to modulate Ca$^{2+}$ binding to CaM, and consisting of a 7 msec burst of 6.8 MHz sinusoidal waves repeating at 1/sec with 0.05 G peak amplitude, in a portable battery operated device (see FIG. 5A) was used for 15 minutes twice daily, or as needed for pain relief The device was lightweight and patients could easily position the coil directly over the knee, even over clothing. Minimum and maximum VAS scores were obtained at baseline (day 0) and daily for the first 14 days and from day 29 to day 42. All patients received PEMF treatment to day 14. Thereafter, 31 (16 active, 15 sham) at day 35, and 28 (16 active, 12 sham) at day 42, were available for analysis. The devices were well tolerated and no adverse events were reported. The results show PEMF caused a significant decrease in mean maximum VAS to approximately 45% of mean start. VAS for the treated group by the end of day 1, which gradually fell to 55% of mean start VAS (P<0.001). In contrast, there was no significant decrease in mean maximum VAS vs mean start VAS at any time point in the sham group (P=0.555). There was no significant difference in mean start VAS between the active and sham groups (Active=7±0.31, Sham=7.1±0.34, P=0.903). These results are summarized in FIG. 9. Compared to known treatments for OA, this treatment intervention was effective even on a patient population that did not have end stage disease and had to be on their feet at least two hours a day; in addition, the PEMF treatment time was short (e.g., 15 minutes), and use did not interfere with work or off-work activities. It has been proposed that CaM-dependent NO release can orchestrate OA pain relief by increasing circulation, decreasing nerve irritation, and decreasing inflammation, The rapid onset response in the active group is remarkably similar to that reported for a similar PEMF signal which produced a 3-fold reduction in pain from breast reduction surgery within 5 hours post-op (Rohde et al., Plastic Reconst Surg. 2009). That study also showed IL-1β, a master inflammatory cytokine, was also reduced by 3-fold in the wound bed by PEW within the same post-op me. This supports a mechanism of action of PEMF in this study that is anti-inflammatory, caused by a PENH signal chosen a priori, according to the devices and methods described herein, to modulate the CaM/constitutive nitric oxide synthase (cNOS) pathway which produces an initial rapid and transient release of NO leading to vaso and lymph dilatation, This could cause a rapid reduction of effusion (edema) with the concomitant rapid reduction of pain observed here. It may also be an effect that the mechanism of PEMF effect involved the down-regulation of IL-1β, with its consequent effect on inflammation, in this patient population.

While the devices, apparatus and method have been described herein in terms of what are presently considered to be the most practical and preferred embodiments, it is to be understood that the disclosure need not be limited to the disclosed embodiments. This disclosure is intended to cover various modifications and similar arrangements included within the spirit and scope of the disclosure, encompassing modifications and similar structures.

What is claimed is:
1. A method of treating degenerative joint disease comprising:
    positioning a flexible coil wire applicator of a lightweight wearable or stationary pulsed EMF therapy device adjacent to a joint or tissue to be treated;

applying a treatment regime from the therapy device, wherein the treatment regime comprises bursts of electromagnetic signals having a peak amplitude of less than about 200 milliGauss, wherein the bursts have a duration of between about 0.5 msec and about 50 msec, further wherein the bursts are repeated at an interburst interval of between about 2 seconds and 0.1 second for a treatment on-time, followed by a treatment off-time that is greater than the treatment on-time.

2. The method of claim 1, wherein the treatment regime is configured according to a mathematical model.

3. The method of claim 2, wherein the mathematical model is one of a signal to noise ratio (SNR) or power signal to noise ratio (PSNR) in respect to calcium binding to calmodulin, and in further respect to calmodulin-dependent NO signaling.

4. The method of claim 2, wherein the mathematical model is one of a signal to noise ratio (SNR) or power signal to noise ratio (PSNR) in respect to the asymmetrical kinetics of ion binding to intracellular buffers to increase the rate of calcium binding in further respect to calmodulin-dependent signaling.

5. The method of claim 1, wherein the treatment regime is configured to incorporate asymmetrical kinetics of ion binding to intracellular buffers to increase the rate of ion binding and enhance a biochemical signaling pathway employed for growth, repair or maintenance.

6. The method of claim 5, wherein the treatment regime is configured to accelerate $Ca^{2+}$ binding to intracellular calcium buffers, such as CaM.

7. The method of claim 1, wherein the treatment regime is configured to modulate CaM-dependent signaling for cytokine and growth factor production in vivo.

8. The method of claim 1, wherein the treatment regime is configured to modulate CaM-dependent NO signaling.

9. The method of claim 1 for the treatment of osteoarthritis.

10. The method of claim 1 for the treatment of rheumatoid arthritis.

11. The method of claim 1 for the treatment of spondyloarthritis.

12. The method of claim 1 for the treatment of arthritis.

13. The method of claim 1, wherein the treatment on-time is between about 1 minute and about 60 minutes.

14. The method of claim 1, wherein the treatment on-time is approximately 15 minutes.

15. The method of claim 1, wherein the treatment on-time is approximately 5 minutes.

16. The method of claim 1, wherein the treatment off-time is between about 15 minutes and about 23 hours.

17. The method of claim 1, wherein the treatment off-time is approximately 11 hours.

18. The method of claim 1, wherein the interburst interval is approximately 1 second.

19. The method of claim 1, wherein the interburst interval is approximately 0.5 second.

20. The method of claim 1, wherein the bursts have a duration of approximately 7 msec.

21. The method of claim 1, wherein the bursts have a duration of approximately 2 msec.

22. The method of claim 1, wherein the electromagnetic waves within the burst have a carrier frequency of about 6.8 MHz.

23. The method of claim 1, wherein the electromagnetic waves within the burst have a carrier frequency of about 27.12 MHz.

24. The method of claim 1, wherein the pulse of electromagnetic waves within the burst have a duration of about 0.5 μsec.

25. A method of treating degenerative joint disease comprising:
positioning a flexible coil wire applicator of a lightweight, wearable battery-operated EMF therapy device adjacent to a joint or tissue to be treated;
treating the joint or tissue by applying bursts of electromagnetic waves having a peak amplitude of less than about 200 milliGauss from the therapy device, wherein the bursts have a duration of between about 0.5 msec and about 50msec, further wherein the bursts are repeated at an interburst interval of between about 10 seconds and 0.1 second for a treatment on-time of between about 5 minutes and 30 minutes, followed by a treatment off-time that is greater than about 30 minutes.

26. The method of claim 25, wherein treating the joint or tissue comprises applying bursts of 6.8 MHz sinusoidal electromagnetic waves having a peak amplitude of about 50milliGauss, wherein the duration of the burst is about 7 msec, and bursts repeat approximately every second.

27. A method of treating degenerative joint disease comprising:
applying a coil applicator of a lightweight wearable or stationary pulsed EMF therapy device adjacent to a joint or tissue to be treated;
applying a treatment regime from the therapy device, wherein the treatment regime comprises bursts of electromagnetic waves having a peak amplitude of less than about 200 milliGauss, wherein the bursts have a duration of between about 0.5msec and about 50 msec, further wherein the bursts are repeated at an interburst interval of between about 2 seconds and 0.1 second for a treatment on-time, followed by a treatment off-time that is greater than the treatment on-time.

28. The method of claim 27, wherein applying the coil applicator comprises applying a brace or garment incorporating the applicator.

29. The method of claim 27, wherein the coil applicator is applied in conjunction with pharmacological agents such as glucosamine.

\* \* \* \* \*